(12) United States Patent
Erbs et al.

(10) Patent No.: US 8,513,018 B2
(45) Date of Patent: Aug. 20, 2013

(54) IMMORTALIZED AVIAN CELL LINES

(75) Inventors: Philippe Erbs, Dagneux (FR); Marina Kapfer, Castelnau d'Estretefonds (FR); Nathalie Silvestre, Ergersheim (FR)

(73) Assignee: Transgene S.A., Illkirch (FR)

( * ) Notice: Subject to any disclaimer, the term of this patent is extended or adjusted under 35 U.S.C. 154(b) by 0 days.

(21) Appl. No.: 13/482,144

(22) Filed: May 29, 2012

(65) Prior Publication Data

US 2012/0238000 A1    Sep. 20, 2012

Related U.S. Application Data

(60) Division of application No. 12/829,773, filed on Jul. 2, 2010, which is a continuation-in-part of application No. 12/667,240, filed as application No. PCT/EP2008/058472 on Jul. 2, 2008.

(30) Foreign Application Priority Data

Jul. 3, 2007  (EP) .................................... 07360030

(51) Int. Cl.
    *C12N 15/85* (2006.01)
    *C12P 21/00* (2006.01)

(52) U.S. Cl.
    USPC ......................................... 435/455; 435/70.1

(58) Field of Classification Search
    None
    See application file for complete search history.

(56) References Cited

U.S. PATENT DOCUMENTS

| 5,879,924 A | 3/1999 | Foster et al. |
| 6,596,533 B1 | 7/2003 | Erbs et al. |

FOREIGN PATENT DOCUMENTS

| WO | WO 99/54481 A1 | 10/1999 |
| WO | WO 2005/007840 A1 | 1/2005 |
| WO | WO 2005/007857 A1 | 1/2005 |
| WO | WO 2005/042728 A2 | 5/2005 |
| WO | WO 2009/004016 A1 | 1/2009 |

OTHER PUBLICATIONS

P. Erbs et al., In Vivo Cancer Gene Therapy by Adenovirus-mediated Transfer of a Bifunctional Yeast Cytosine Deaminase/Uracil Phosphoribosyltransferase Fusion Gene, 60 Cancer Research 3813-3822 (Jul. 15, 2000).
Z. Ezzeddine et al., Selective Killing of Glioma Cells in Culture and in Vivo by Retrovirus Transfer of the Herpes Simplex Virus Thymidine Kinase Gene, 3(6) the New Biologist 608-614 (Jun. 1991).
F. Fallaux et al., New Helper Cells and Matched Early Region 1-Deleted Adenovirus Vectors Prevent Generation of Replication-Competent Adenoviruses, 9 Human Gene Therapy 1909-1917 (Sep. 1, 1998).
F. Graham et al., Characteristics of a Human Cell Line Transformed by DNA from Human Adenovirus Type 5, 36 Journal of General Virology 59-72 (1977).
C. Guilhot et al., The 12S adenoviral E1A protein immortalizes avian cells and interacts with the avian RB product, 8 Oncogene 619-624 (1993).
I. Ivanov et al., Establishment and characterization of a permanent duck embryo cell line, Experimental Pathology and Parasitology (Apr. 2000).
I. Ivanov et al., Propagation of avian pox virus vaccine strains in duck embryo cell line—Dec. 1999, Experimental Pathology and Parasitology (Apr. 2001).
F. Moolten, Tumor Chemosensitivity Conferred by Inserted Herpes Thymidine Kinase Genes: Paradigm for a Prospective Cancer Control Strategy, 46 Cancer Research 5276-5281 (Oct. 1986).
C. Mullen et al., Transfer of the bacterial gene for cytosine deaminase to mammalian cells confers lethal sensitivity to 5-fluorocytosine: A negative selection system, 89 Proceedings of the National Academy of Sciences of the United States 33-37 (Jan. 1992).

*Primary Examiner* — Celine Qian
(74) *Attorney, Agent, or Firm* — Buchanan Ingersoll & Rooney, PC

(57) ABSTRACT

This invention relates to immortalized avian cells, including those deposited under accession numbers 09070701, 09070702, and 09070703 at the ECACC, and to the use of these cells for the production of viruses. The cells according to the invention are particularly useful for the production of recombinant viral vectors which can be used for the preparation of therapeutic and/or prophylactic compositions for the treatment of animals and more particularly humans.

6 Claims, 10 Drawing Sheets

Random Insertion

Targeted Insertion

IMMORTALIZED AVIAN CELL LINES

CROSS-REFERENCE TO RELATED APPLICATIONS

Figure 1:
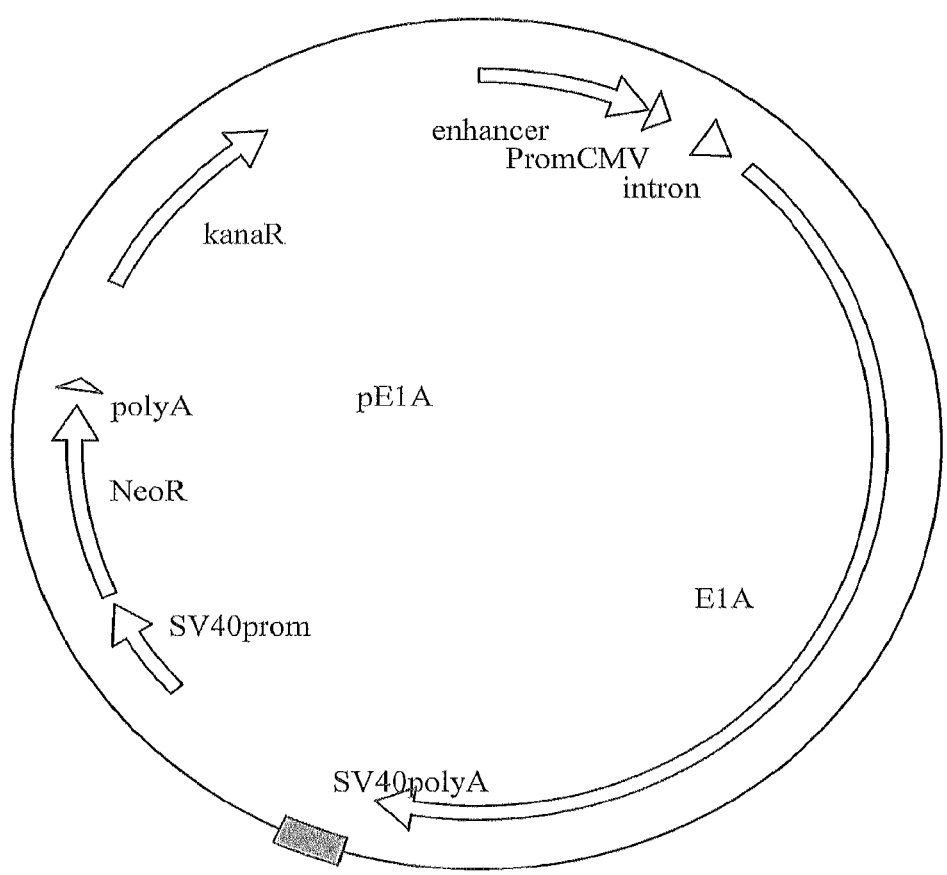

This application is a Divisional application of U.S. patent application Ser. No. 12/829,773, filed on Jul. 2, 2010, which is a Continuation-In-Part application of U.S. patent application Ser. No. 12/667,240, filed on Dec. 30, 2009, which is a U.S. National Stage of PCT/EP2008/058472, filed on Jul. 2, 2008, which designated the United States and was published in the English language on Jan. 8, 2009, as WO 2009/004016 A1 and claims priority under 35 U.S.C. §119 to EP 07360030.6, filed on Jul. 3, 2007; and the content of each is hereby expressly incorporated by reference in their entireties for all purposes and each is assigned to the assignee hereof.

BACKGROUND OF THE INVENTION

1. Technical Field of the Invention

This invention relates to immortalized avian cells, and to the use of these cells for the production of viruses. The cells according to the invention are particularly useful for the production of recombinant viral vectors which can be used for the preparation of therapeutic and/or prophylactic compositions for the treatment of animals and more particularly humans.

2. Description of Background and/or Related Art

Eukaryotic cell lines are fundamental for the manufacture of viral vaccines and many products of biotechnology. Biologicals produced in cell cultures include enzymes, hormones, immunobiologicals (monoclonal antibodies, interleukins, lymphokines), and anticancer agents. Although many simpler proteins can be produced using bacterial cells, more complex proteins that are glycosylated, currently must be made in eukaryotic cells.

Avian cells have been used for years for the production of viral vectors. For example, the Vaccinia virus used for preparing prophylactic composition for the treatment of Variola was cultivated on Chicken Embryonic Fibroblast (CEF). Avian cells are particularly useful since many virus used in pharmaceutical composition are able to replicate on them. More noticeably, various viruses are only able to grow on avian cells. This is for example the case of Mammalian Virus Ankara (MVA) which is unable to grow on mammalian cells. This poxvirus, which derived from a Vaccinia Virus by more than 500 passages on CEF, was used in the early seventies for vaccinating immunodeficient peoples against Variola. Now, MVA is mainly used as a vector for gene therapy purposes. For example, MVA is used as a vector for the MUC1 gene for vaccinating patients against tumor expressing this antigen (Scholl et al., 3 J BIOMED BIOTECHNOL. 194-201 (2003)). MVA carrying the gene coding HPV antigens are also used as a vector for the therapeutic treatment of ovarian carcinoma. More recently, MVA has been the vector of choice for preparing prophylactic treatment against newly emerging diseases or probable biological weapons such as west nile virus and anthrax.

With this respect, there is a growing need for virus production. For now, the most used MVA production process comprises a virus replication step on CEF. However the use of CEF is linked to various difficulties. Firstly, the preparation of CEF comprised many steps which have to be done manually. Furthermore, this virus production process depends on the availability of eggs which may be totally disrupted in case of contamination of the breedings. This problem is more and more relevant with the spread of Avian Flu.

Additionally, many CEFs possess a reverse transcriptase activity (RT). RT is an enzyme necessary for retroviruses to reproduce. Retroviruses are found in many different species. RT is not infectious in humans or animals, and it has not been shown to cause any adverse health effects in people. Using a highly sensitive polymerase chain reaction (PCR) based assay, RT activity has been detected in minute quantities in vaccines manufactured with chick embryo fibroblasts. The source of the enzyme is probably a partial viral genome coding for RT, believed to be integrated into chick cells hundreds or thousands of years ago. Avian retroviruses that produce this RT are not known to affect humans. While the human immunodeficiency virus (HIV, the virus that leads to AIDS), is a retrovirus, the RT activity detected in vaccines is definitively not derived from HIV. Furthermore, the presence of RT does not confirm the presence of a retrovirus. Nevertheless, a cell line with no endogenous RT activity would be of interest.

In order to emancipate virus production process from the use of CEF, there is an increasing need for an avian cell line which would allow the replication and the production of the virus. Immortalized cell lines can be maintained or frozen from batch to batch on the production site and are always available for a new production process. Moreover as they are confined at the production plant, they are less subject to contamination by exogenous contaminant. Their use allows a drastic reduction of the manual manipulation needed for the production process. All these properties lead to a reduction of the price and of the duration of the production process as well as a diminution of the potential contamination.

Finally, cell lines can be fully characterized and are thus totally compliant with the good laboratory practice and the requirements of the different medical agencies.

Different avian cell lines have already been described. For example, DF1 (U.S. Pat. No. 5,879,924) is a spontaneously immortalized chicken cell line derived from 10 day old East Lansing Line (ELL-0) eggs. The cells are useful as substrates for virus propagation, recombinant protein expression and recombinant virus production. However, this cell line is susceptible to various virus such as Meleagrid herpesvirus 1 (Herpes Virus of Turkey), Fowlpox Virus, reovirus, Avian Sarcoma Leukemia Virus and Rous Sarcoma Virus.

Immortal avian cells can also be derived from embryonic stem cells by progressive severance from growth factors and feeder layer, thus maintaining growth features and infinite lifespan characteristic of undifferentiated stem). The only available avian cell line derived by this process is the Ebx chicken cell line (WO 2005/007840) which has been in contact with feeder layers from murin origin, raising additional regulatory questions like murin virus contamination and presence of endogenous retroviral sequences in chicken cells. Moreover this cell lines have been described in some conditions as unstable and differentiation-prone.

A duck embryo permanent cell line, free from endogenous avian retroviruses has also been established. The cell line, designated as DEC 99 (Ivanov et al. EXPERIMENTAL PATHOLOGY AND PARASITOLOGY, April 2000 Bulgarian Academy of Sciences) has been cultured over 140 consecutive passages and it is not tumorigenic for birds. The DEC 99 cell line is a standard cell culture system that has been used for research and can be applied for the needs of biotechnology. This cell line is a suitable model for studies in the field of cell biology, virology, immunology, toxicology and for the production of diagnostics and vaccines. The susceptibility of the permanent duck embryo cell line (CL) DEC 99 to infection with embryo-adapted avian poxvirus (APV) vaccine strains have been studied (Ivanov et al. EXPERIMENTAL PATHOLOGY AND PARASITOLOGY, Apr. 6 2001 Bulgarian Academy of Sciences). The FK and Dessau vaccine strains of fowl and pigeon origin respectively have been used. The virus strains were consecutively passaged (13 passages) on primary duck embryo cell cultures (CCs). The adapted virus strains have been further passaged (12 passages) in the CCs of the DEC 99 cell line, where a typical cytopathic effect (CPE) was observed. The production of infectious virions was checked by inoculation of 11-day-old White Leghorn embryos, where typical pox proliferations on the chorioalantoic membranes (CAMs) were formed. In the DEC 99 cells the FK strain caused early CPE, compared to the Dessau strain and reached a titer of 106,25 CCID50/ml. The DEC 99-adapted virus strains induced typical cutaneous "takes" after vaccination of two-month-old chicks. Thus, the DEC 99, as a standard CC system appears to be suitable for production of vaccines against fowl pox. Nevertheless this particular cell line is slow growing after passage 40 and is unable to grow in suspension.

Nucleic acid sequences from the Early region of human Adenovirus 5 have already been used to transform some specific human cells in vitro (293 and PER. C6 cell lines; Fallaux, F. J. et al., 9 HUM. GENE THER. 1909-17 (1998); Graham, F. L. et al., 36 J. GEN. VIROL. 59-74 (1977)).

In general terms, the adenoviral genome consists of a double-stranded linear DNA molecule approximately 36 kb in length which contains the sequences coding for more than 30 proteins. At each of its ends, a short inverted sequence of 100 to 150 nucleotides, depending on the serotypes, designated ITR (inverted terminal repeat), is present. ITRs are involved in the replication of the adenoviral genome. The encapsidation region of approximately 300 nucleotides is located at the 5' end of the genome immediately after the 5' ITR.

The early genes are distributed in 4 regions which are dispersed in the adenoviral genome, designated E1 to E4 (E denoting "early"). The early regions comprise at least six transcription units which possess their own promoters. The expression of the early genes is itself regulated, some genes being expressed before others. Three regions, E1, E2 and E4, respectively, are essential to the viral replication. Thus, if an adenovirus is defective for one of these functions, that is to say if it cannot produce at least one protein encoded by one of these regions, this protein will have to be supplied to it in trans.

The E1 early region is located at the 5' end of the adenoviral genome, and contains 2 viral transcription units, E1A and E1B, respectively. This region codes for proteins which participate very early in the viral cycle and are essential to the expression of almost all the other genes of the adenovirus. In particular, the E1A transcription unit codes for a protein which trans-activates the transcription of the other viral genes, inducing transcription from the promoters of the E1B, E2A, E2B and E4 regions.

It was shown by Guilhot et al. (Guilhot, C. et al., 8 ONCOGENE 619-24 (1993)) that retroviral transduction of the 12S protein of E1A from Ad5 can lead to immortalization of quail cells. However, WO 200/5042728 disclosed that it is impossible to immortalize avian cells when the E1A gene is introduced by transfection of naked DNA instead of retrovirus infection. WO 2005/042728 further states: "that the extremely efficient and stable transduction via retrovirus infection creates a cell pool large enough to harbor individual cells with spontaneous genomic changes that have blocked apoptosis that normally is induced upon Retinoblastoma inactivation." (page 10).

The presence of retroviral sequences in the cells obtained by Guilhot et al. hinder the use of such cells for the production of biological product and more particularly for therapeutic compounds.

BRIEF SUMMARY OF THE INVENTION

The inventors have surprisingly found that avian cells, and more particularly *cairina moschata* cells, can be efficiently immortalized by E1A transfection with a non-viral vector.

In order to solve the different problems linked to the use of CEF and/or to the use of previously available cell lines, the present invention provides an immortalized avian cell comprising an E1A nucleic acid sequence characterized in that said cell is obtained by a process comprising the step of transfecting the cell with a non viral vector comprising said E1A nucleic acid sequence and wherein said cell does not comprise an E1B nucleic acid sequence.

The present invention also refers to a process for immortalizing an avian cell comprising the step of transfecting said cell with a non-viral vector comprising an E1A nucleic acid sequence and wherein said process does not comprise a step of transfecting said cell with an E1B nucleic acid sequence.

The present invention includes immortalized avian cell lines deposited at the European Collection of Cell Cultures (ECACC) under accession numbers 09070701, 09070702, and 09070703 and derivatives thereof. The immortalized avian cells may further comprise one or more nucleic acid sequences that allow propagation of a defective virus. The immortalized avian cells may further comprise a nucleic acid coding a substance of interest. The immortalized avian cell lines may be used for the replication of a virus, including live, attenuated, or recombinant viruses. The virus to be replicated using the immortalized avian cell lines may be poxvirus (such as vaccinia virus, e.g., a modified vaccinia virus Ankara (MVA)), adenovirus, retrovirus, herpervirus, alphavirus, foamy virus, and adenovirus-associated virus.

Other characteristics, aspects, and advantages of the invention are set forth in the detailed description that follows.

DETAILED DESCRIPTION OF THE FIGURES

FIG. 1: Vector comprising a gene coding the E1A nucleic acid sequence.

Figure 2:
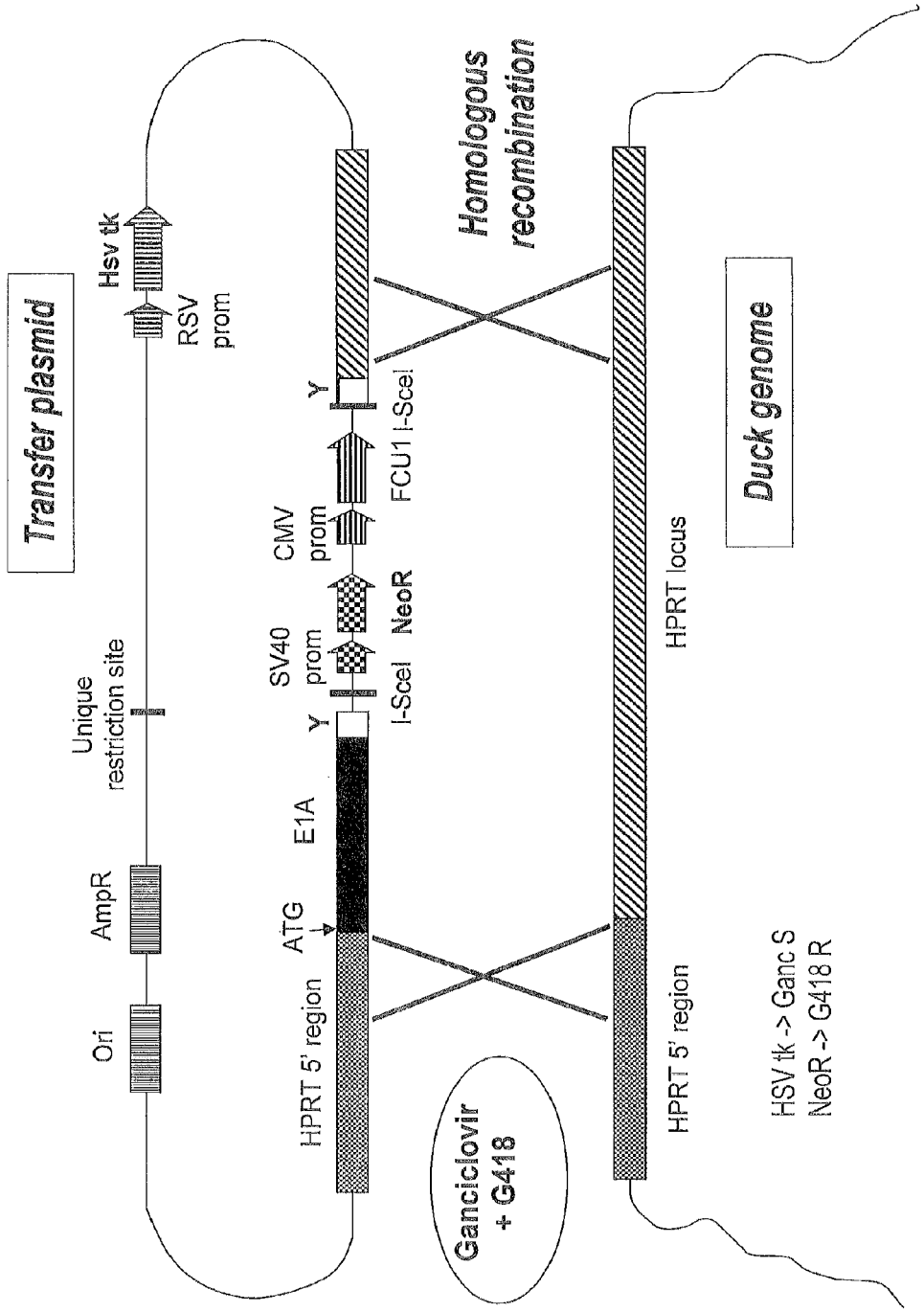

FIG. 2: Schematic representation of the site specific insertion of the E1A nucleic acid sequence into the HPRT gene.

Figure 3:
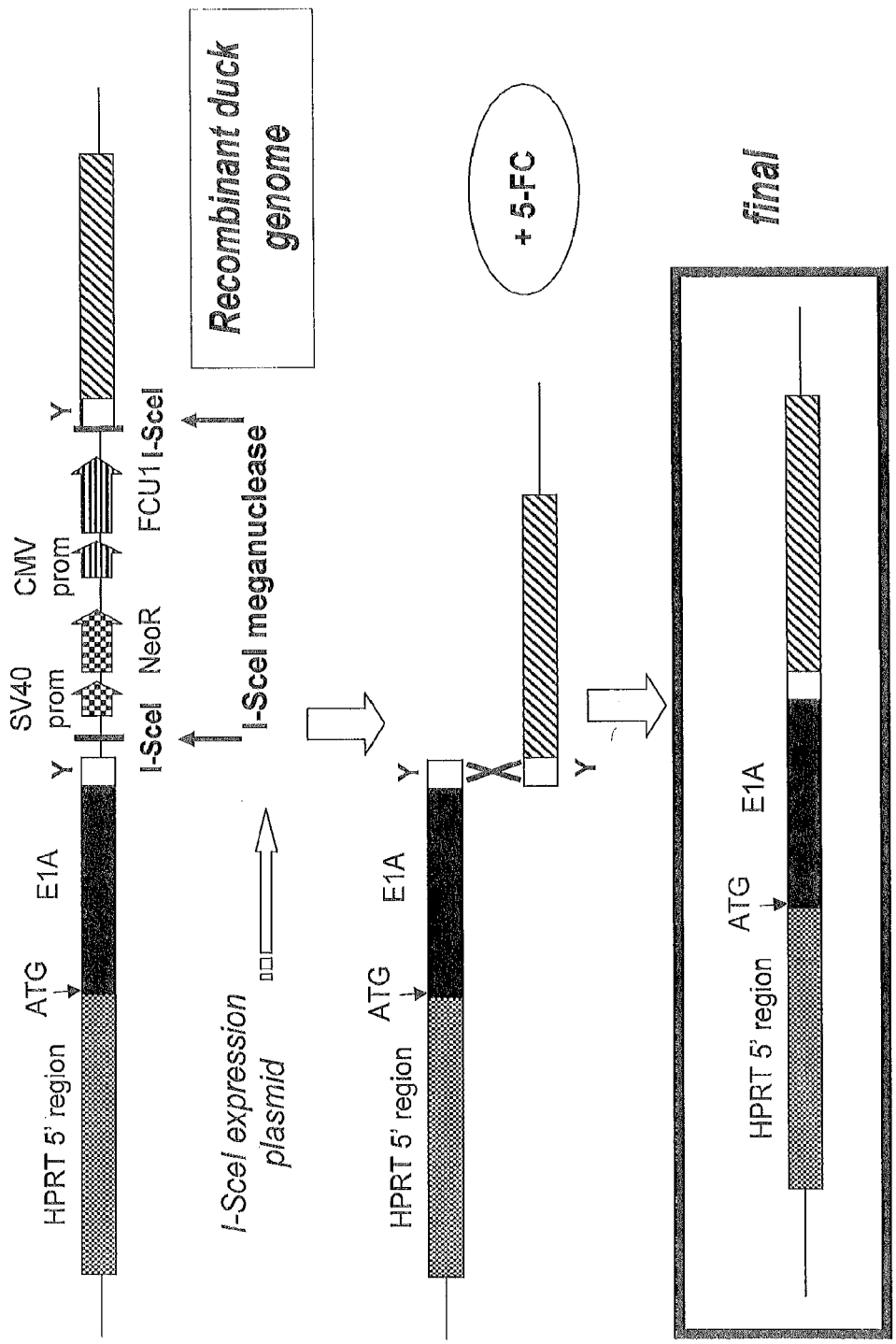

FIG. 3: Schematic representation of the elimination of the first and the third selection marker from the genome of the immortalized cell obtained by the process of the invention.

Figure 4:
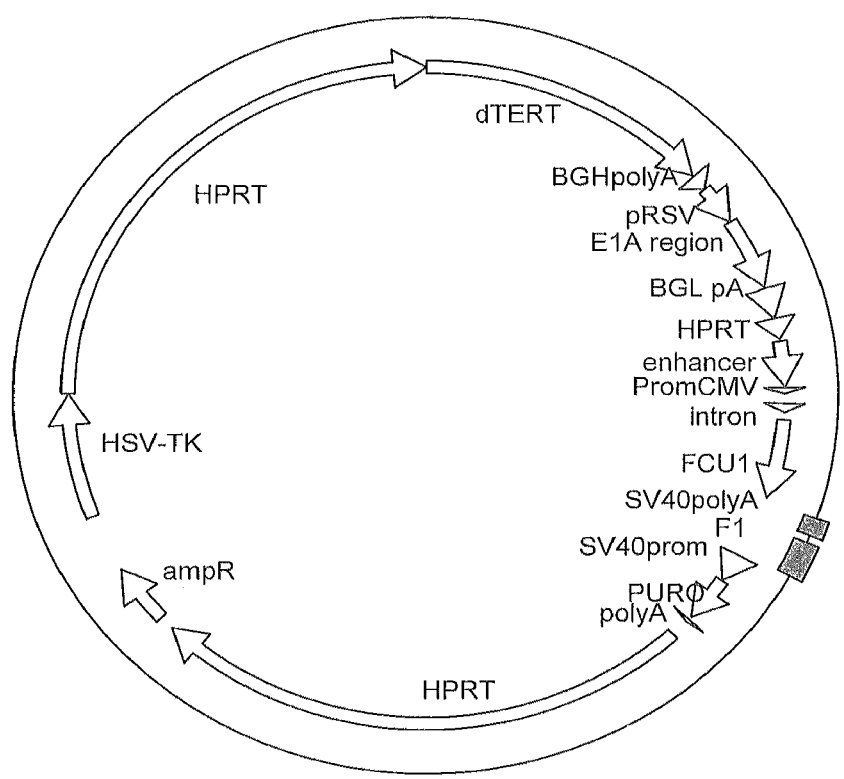

FIG. 4: Vector comprising a gene coding the *Cairina moschata* telomerase reverse transcriptase gene and the E1A nucleic acid sequence.

Figure 5:
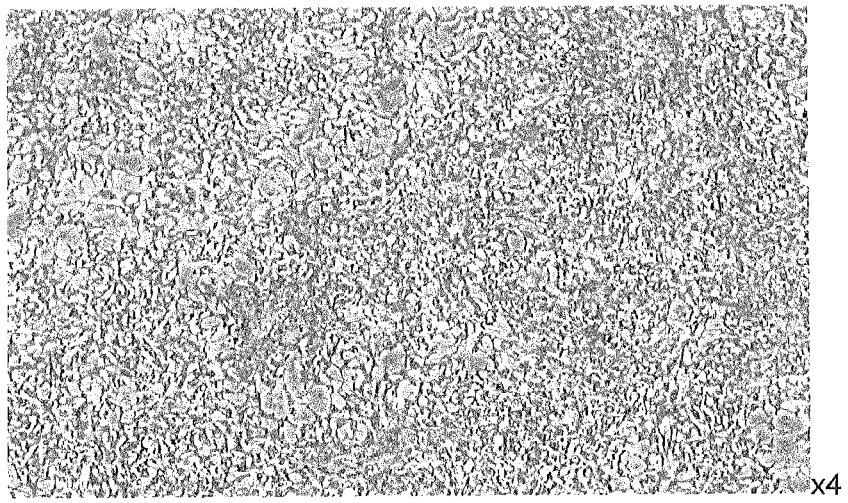
Figure 5:
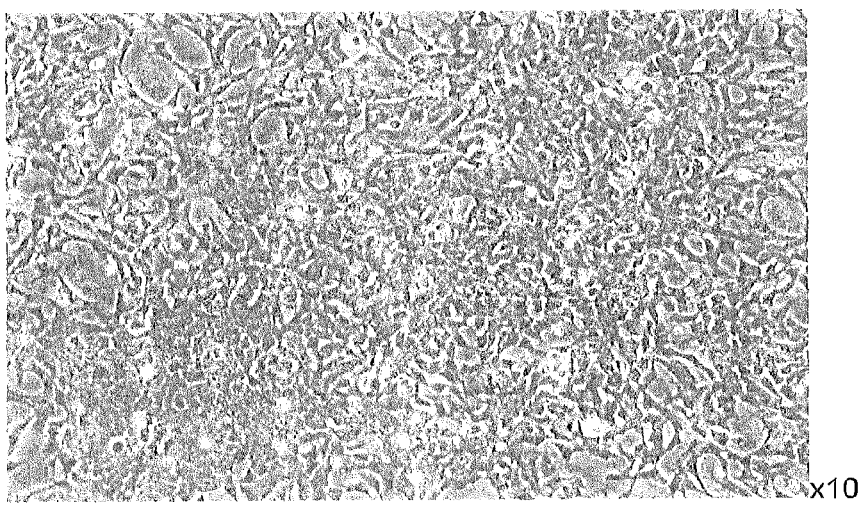
Figure 5:
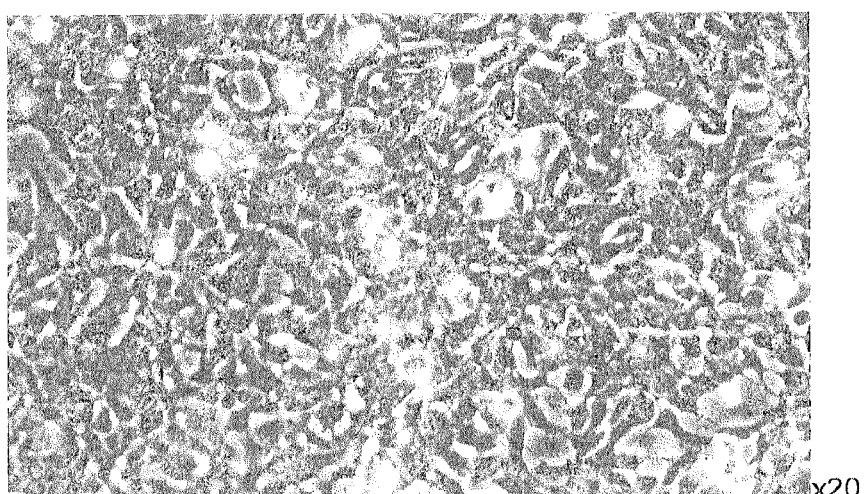

FIG. 5: Light microscopy imaging of the *Cairina moschata* immortalized avian cell line ECACC 09070701 (passage 21).

Figure 6:
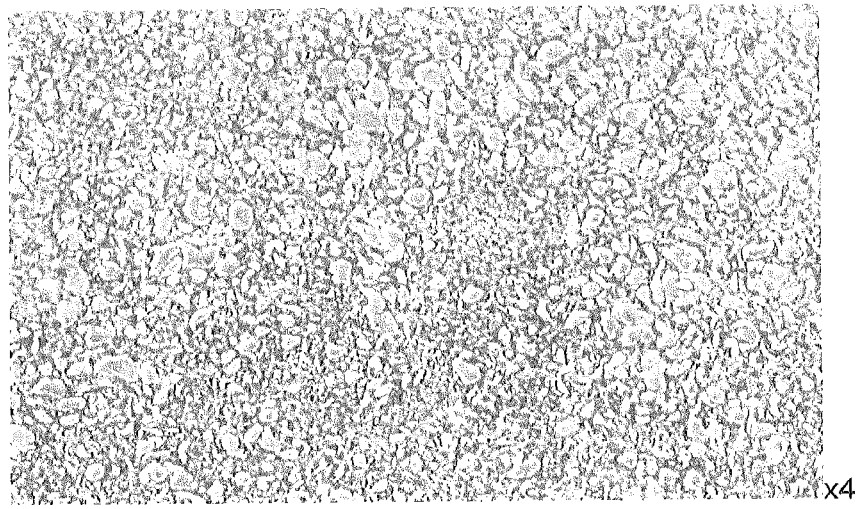
Figure 6:
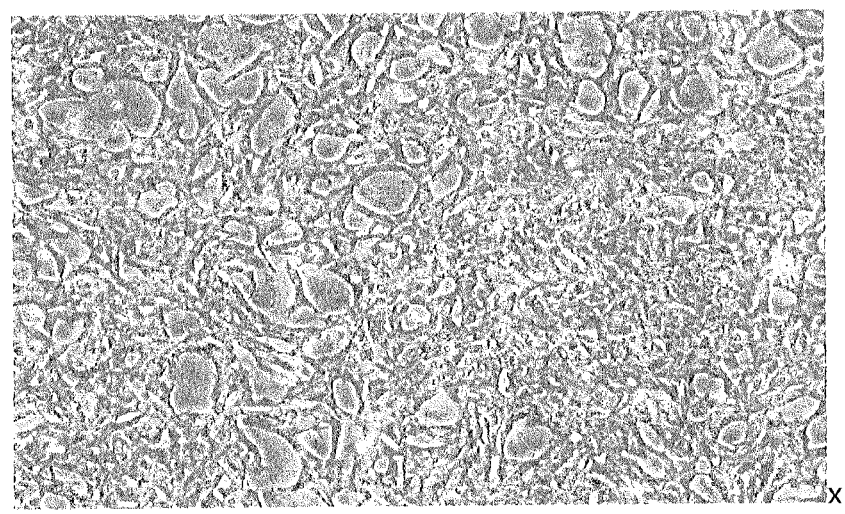
Figure 6:
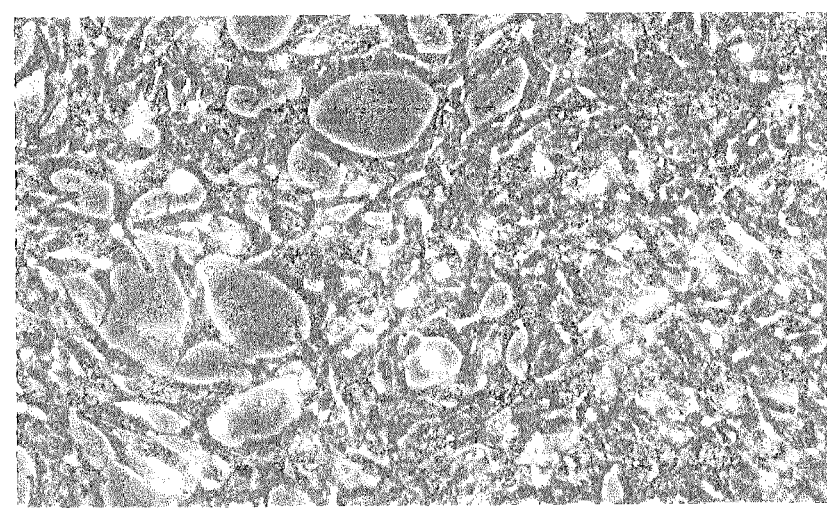

FIG. 6: Light microscopy imaging of the *Cairina moschata* immortalized avian cell line ECACC 09070702 (passage 24).

Figure 7:
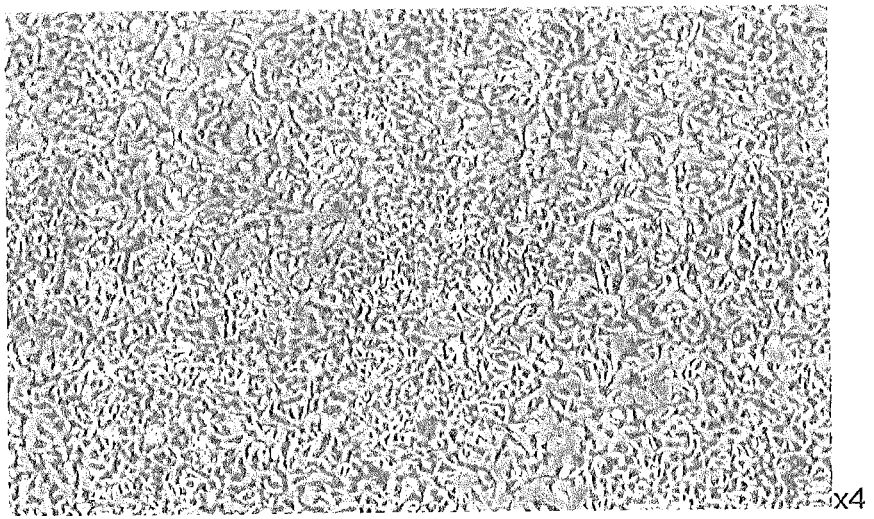
Figure 7:
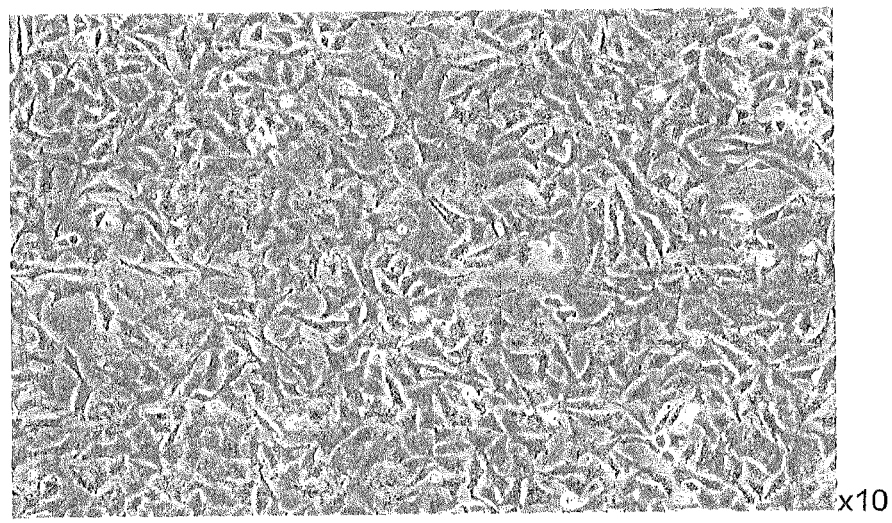
Figure 7:
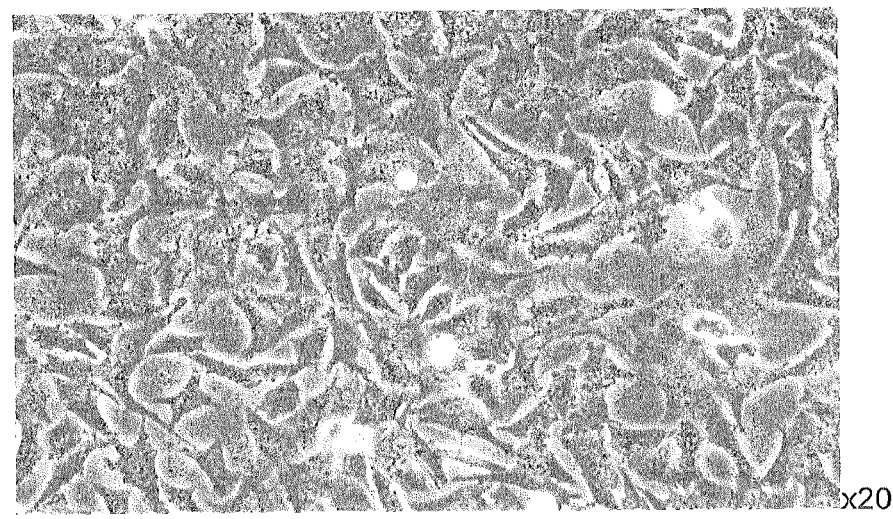

FIG. 7: Light microscopy imaging of the *Cairina moschata* immortalized avian cell line ECACC 09070703 (passage 28).

Figure 8:
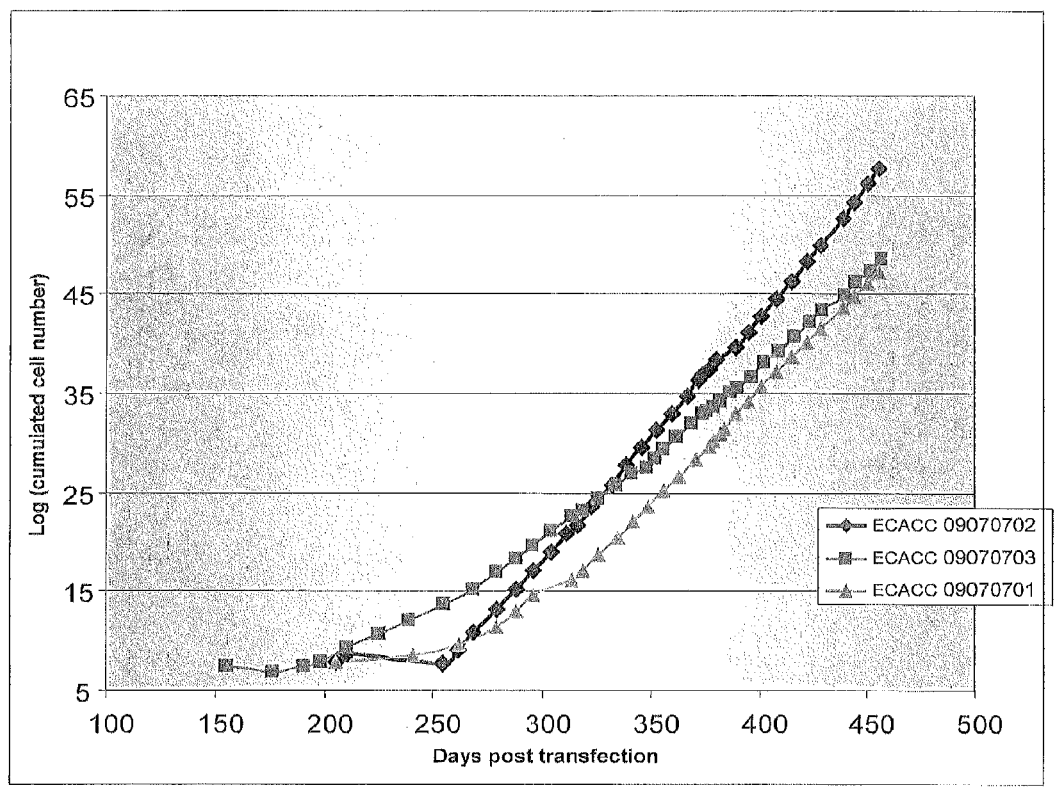

FIG. 8: *Cairina moschata* immortalized avian cell line ECACC 09070701, ECACC 09070702, and ECACC 09070703 growth curve.

Figures 9A, 9B, 9C:
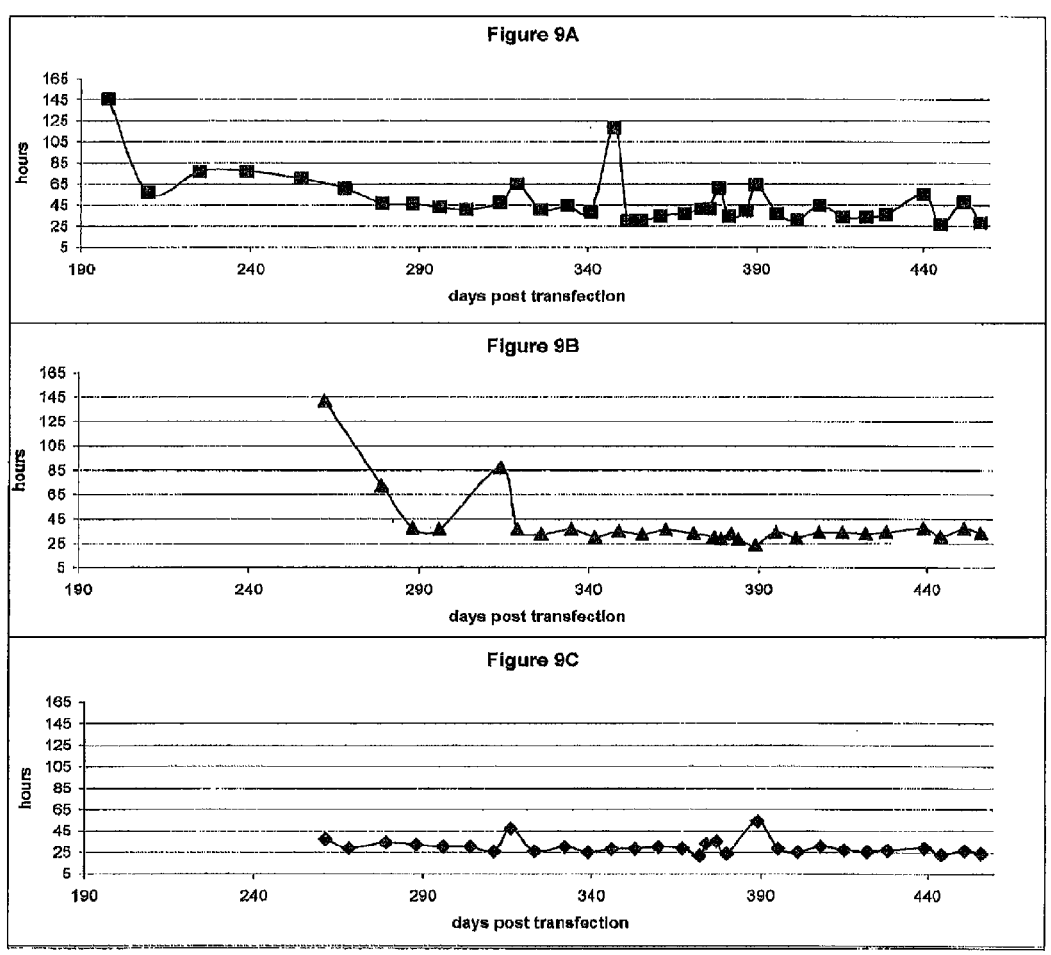

FIG. 9: *Cairina moschata* immortalized avian cell line ECACC 09070703 (FIG. 9A), ECACC 09070701 (FIG. 9B), and ECACC 09070702 (FIG. 9C) population doubling time evolution.

Figure 10:
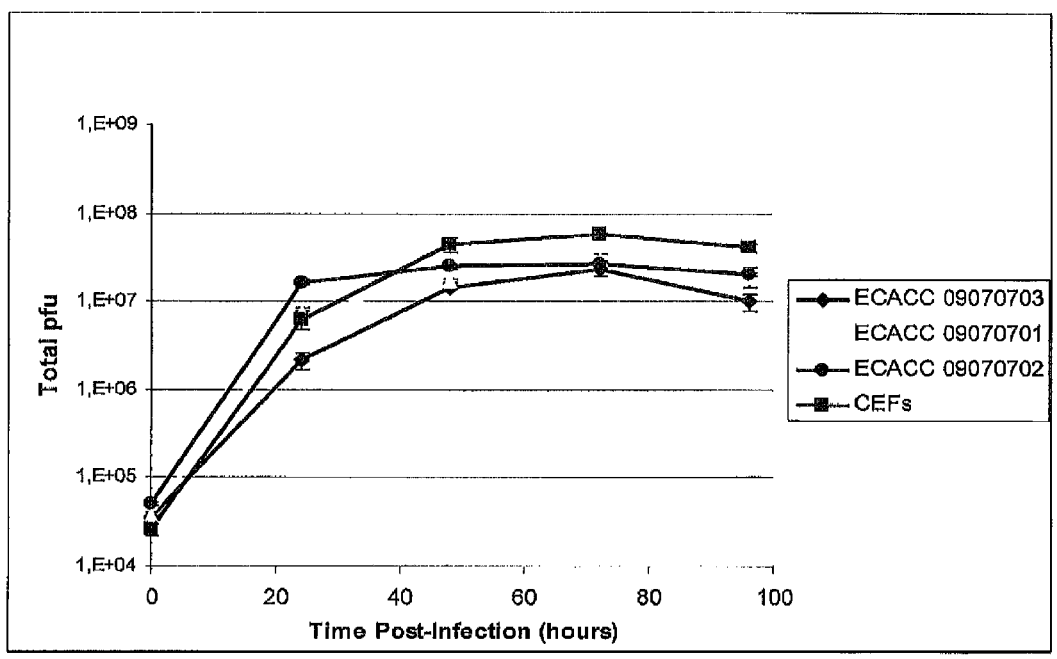

FIG. 10: Production of Modified Vaccinia virus Ankara (MVA) in the *Cairina moschata* immortalized avian cell line ECACC 09070701, ECACC 09070702, and ECACC 09070703 (MOI 0.05).

DETAILED DESCRIPTION OF THE INVENTION

The inventors have surprisingly found that avian cells, and more particularly *cairina moschata* cells, can be efficiently immortalized by E1A transfection with a non-viral vector.

In order to solve the different problems linked to the use of CEF and/or to the use of previously available cell lines, the present invention provides an immortalized avian cell comprising an E1A nucleic acid sequence characterized in that said cell is obtained by a process comprising the step of transfecting the cell with a non viral vector comprising said E1A nucleic acid sequence and wherein said cell does not comprise an E1B nucleic acid sequence.

The present invention also refers to a process for immortalizing an avian cell comprising the step of transfecting said cell with a non-viral vector comprising an E1A nucleic acid sequence and wherein said process does not comprise a step of transfecting said cell with an E1B nucleic acid sequence.

The present invention includes immortalized avian cell lines deposited at the European Collection of Cell Cultures (ECACC) under accession numbers 09070701, 09070702, and 09070703 and derivatives thereof. The immortalized avian cells may further comprise one or more nucleic acid sequences that allow propagation of a defective virus. The immortalized avian cells may further comprise a nucleic acid coding a substance of interest. The immortalized avian cell lines may be used for the replication of a virus, including live, attenuated, or recombinant viruses. The virus to be replicated using the immortalized avian cell lines may be poxvirus (such as vaccinia virus, e.g., a modified vaccinia virus Ankara (MVA)), adenovirus, retrovirus, herpervirus, alphavirus, foamy virus, and adenovirus-associated virus.

An immortalized cell, as used herein, refers to a cell capable of growing in culture for more than 35 passages.

The term passage number refers to the number of times that a cell population has been removed from the culture vessel and undergone a subculture (passage) process, in order to keep the cells at a sufficiently low density to stimulate further growth.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or", and "all or any other combination of the elements connected by said term".

As used herein, the term "comprising" is intended to mean that the products, compositions and methods include the referenced components or steps, but not excluding others. "Consisting essentially of" when used to define products, compositions, and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "E1A nucleic acid sequence" refers to nucleic acid sequence all gene products of the adenovirus E1A region, including the nucleic acid sequence coding the two major RNAs: 13S and 12S.

Preferably, the term "E1A nucleic acid sequence" refers to a nucleic acid sequence comprising a nucleic acid sequence which has at least 60% amino acid sequence identity to SEQ ID NO:1. In a more preferred embodiment of the invention, E1A refers to a nucleic acid sequence comprising a nucleic acid sequence which has at least 70%, preferably at least 80%, and even more preferably at least 90%, nucleic acid sequence identity to SEQ ID NO:1. In a more preferred embodiment, E1A refers to the nucleic acid sequence set forth in SEQ ID NO:1.

As used herein, the term "E1B nucleic acid sequence" refers to all nucleic acid sequence of the adenovirus E1B region, including the nucleic acid sequence coding the 3 major polypeptides, of 19 kd and 55 kd.

As employed herein, the term "substantially the same nucleic acid sequence" refers to nucleic acid molecule having sufficient identity to the reference polynucleotide, such that it will hybridize to the reference nucleotide under moderately stringent hybridization conditions. In one embodiment, nucleic acid molecule having substantially the same nucleotide sequence as the reference nucleotide sequence set forth in SEQ ID NO:1.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5*Denhart's solution, 5*SSPE, 0.2% SDS at 42° C., followed by washing in 0.2*SSPE, 0.2% SDS, at 65° C.

As used herein, the expression "non-viral vector" notably refers to a vector of plasmid origin, and optionally such a vector combined with one or more substances improving the transfectional efficiency and/or the stability of said vector and/or the protection of said vector in vivo toward the immune system of the host organism. These substances are widely documented in the literature which is accessible to persons skilled in the art (see, e.g., Feigner et al., 32 PROC. WEST. PHARMACOL. SOC. 115-121 (1987); Hodgson and Solaiman, 14 NATURE BIOTECHNOLOGY 339-342 (1996); Remy et al., 5 BIOCONJUGATE CHEMISTRY 647-654 (1994)). By way of illustration, but without limitation, they may be polymers, lipids, in particular cationic lipids, liposomes, nuclear proteins, or neutral lipids. These substances may be used alone or in combination. Examples of such compounds are in particular available in WO 98/08489, WO 98/17693, WO 98/34910, WO 98/37916, WO 98/53853, EP 890362, or WO 99/05183.

A combination which may be envisaged is a plasmid recombinant vector combined with cationic lipids (DOGS, DC-CHOL, spermine-chol, spermidine-chol and the like) and neutral lipids (DOPE).

The choice of the plasmids which can be used in the context of the present invention is vast. They may be cloning and/or expression vectors. In general, they are known to a person skilled in the art and a number of them are commercially available, but it is also possible to construct them or to modify them by genetic engineering techniques. There may be mentioned, by way of examples, the plasmids derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid used in the context of the present invention contains a replication origin ensuring the initiation of replication in a producing cell and/or a host cell (for example, the ColE1 origin may be selected for a plasmid intended to be produced in $E.$ $coli$ and the oriP/EBNA1 system may be selected if it is desired for it to be self-replicating in a mammalian host cell, Lupton and Levine, 5 MOL. CELL. BIOL. 2533-2542 (1985); Yates et al., 313 NATURE 812-815 (1985). It may comprise additional elements improving its maintenance and/or its stability in a given cell (cer sequence which promotes the monomeric maintenance of a plasmid (Summers and Sherrat, 36 CELL 1097-1103 (1984), sequences for integration into the cell genome)).

The term "non-viral vector" excludes viral vectors, such as, for example vector deriving from a poxvirus (vaccinia virus, in particular MVA, canarypox and the like), from an adenovirus, from a retrovirus, from a herpesvirus, from an alphavirus, from a foamy virus or from an adeno-associated virus.

The present invention also relates to cells deriving from the cell according to the invention. As used herein, the term "derived" refers to cells which develop or differentiate from or have as ancestor a cell according to the invention.

The term passage number refers to the number of times that a cell population has been removed from the culture vessel and undergone a subculture (passage) process, in order to keep the cells at a sufficiently low density to stimulate further growth.

As used herein, the term "transfected" refers to the stable transfection or the transient transfection of the cell of the invention.

The term "stable transfection" or "stably transfected" refers to the introduction and integration of foreign nucleic acid sequence into the genome of the transfected cell. The term "stable transfectant" refers to a cell that has stably integrated foreign DNA into the genomic DNA.

According to a preferred embodiment of the invention, the avian cell of the invention derives from a cell of the Anatidae family or of the Phasianidae family. Among Anatidae, cells belonging to the *Cairina* or *Anas* genus are particularly preferred. Even more preferably, the cells according to the invention belong to the *Cairina moschata* or to the *Anas platyrhynchos* species.

Preferably, the cell according to the invention is taken from an embryonic organism. Methods allowing the isolation of cells from a living organism are well known to the one skilled in the art. For example, methods disclosed in Example 2 can be used. According to a preferred embodiment of the invention, the primary cell is isolated from an embryo belonging to the Anatidae family which is between 0 and 20 days old, more preferably between 5 and 15 days old, and even more preferably between 11 and 14 days old.

According to a preferred embodiment of the invention, the E1A nucleic acid sequence is inserted into a target DNA sequence of the cell according to the invention.

As used herein, a "target DNA sequence" is a predetermined region within the genome of a cell which is targeted for modification by homologous recombination with the vector. Target DNA sequences include structural genes (i.e., DNA sequences encoding polypeptides including in the case of eucaryotes, introns and exons), regulatory sequences such as enhancers sequences, promoters and the like, and other regions within the genome of interest. A target DNA sequence may also be a sequence which, when targeted by a vector, has no effect on the function of the host genome.

As used herein, "inserted into a target DNA sequence" widely means that the homologous recombination process which leads to the insertion of the immortalizing gene introduces a deletion or a disruption into the targeted DNA sequence.

To produce immortalized avian cell wherein the E1A nucleic acid sequence is inserted into a target DNA sequence, the vector used in the process according to the invention can further comprise two homologous sequences capable of homologous recombination with a region of a target DNA sequence native to the genome of said cell genome.

The presence of said homologous sequences allows the site specific insertion of the nucleic acid molecule of the invention into the target DNA sequence by homologous recombination.

The term "homologous recombination" refers to the exchange of DNA fragments between two DNA molecules at the site of essentially identical nucleotide sequences. According to this particular embodiment of the invention, within the vector are sequences which are homologous with sequence portions contained within the target DNA sequence. In a preferred embodiment of the invention, the homologous sequences in the transfer vector are hundred percent homologous to the region of the target sequence. However, lower sequence homology can be used. Thus, sequence homology as low as about 80% can be used.

The homologous sequences in the transfer vector comprise at least 25 bp. Longer regions are preferred, at least 500 bp, and more preferably at least 5,000 bp.

According to a more preferred embodiment of the invention, the nucleic acid molecule is surrounded by the homologous sequences in the vector.

As used herein "surrounded" means that one of the homologous sequences is located upstream of the nucleic acid molecule of the invention and that one of the homologous sequences is located downstream of the nucleic acid molecule of the invention. As used herein, "surrounded" does not necessarily mean that the two homologous sequences are directly linked to the 3' or to the 5' end of the immortalizing gene. The immortalizing gene and the homologous sequences can be separated by an unlimited number of nucleotides.

One skilled in the art is able to choose the appropriate homologous sequences in order to target a specific DNA sequence into the genome of the cell to be immortalized. For example, one homologous sequence can be homologous to a part of the targeted sequence, wherein the other homologous sequence is homologous to a DNA sequence located upstream or downstream of the targeted sequence. According to another example, one of the homologous sequences can be homologous to a DNA sequence located upstream of the targeted DNA sequence, wherein the other homologous sequence is homologous to a DNA sequence located downstream of the target DNA sequence. In another example, both the homologous sequences are homologous to sequences located into the target DNA sequence.

According to a preferred embodiment of the invention, the target DNA sequence is the HPRT (Hypoxanthine phosphorybosyl transferase) gene.

The genomic sequence comprising the HPRT promoter and the HPRT gene of *cairina moschata* is set forth in SEQ ID NO:2. The sequence coding the HPRT start at the ATG codon in position 8695 of the nucleic acid sequence set forth in SEQ ID NO:2, the sequence upstream of this ATG codon is the HPRT promoter sequence.

One skilled in the art is able to choose the homologous sequences necessary for the integration of the E1A nucleic acid sequence into the HPRT gene. As between the various members of a family, the genomic sequences coding HPRT are highly homologous. One skilled in the art is also able to design the homologous sequences necessary to target the HPRT gene of every avian cells.

According to a more preferred embodiment of the invention, the homologous sequences are customized in order to insert the E1A nucleic acid sequence downstream of the cell's HPRT promoter. In this particular embodiment, the nucleic acid molecule of the invention is operably linked to the cell's endogenous HPRT promoter. "Operably linked" is intended to mean that the E1A nucleic acid sequence is linked to the promoter in a manner which allows for its expression in the cell.

According to this particular embodiment, the homologous sequence, upstream of the nucleic acid molecule of the invention, has preferably a nucleic acid sequence which is homologous with at least 500 contiguous by and more preferably at least 5,000 contiguous by of the nucleic acid sequence starting from the nucleotide at position 1 and ending with the nucleotide at position 8694 of the nucleic acid sequence set forth in SEQ ID NO:2, with the proviso that said homologous sequence is not homologous with the nucleic acid sequence starting with the nucleotide at position 8695 and ending with the nucleotide at position 26916 of the nucleic acid sequence set forth in SEQ ID NO:2. Moreover, this upstream homologous sequence is preferably directly linked to the start codon of the E1A nucleic acid sequence. According to an even more preferred embodiment of the invention, the homologous sequence upstream the nucleic acid molecule of the invention consists in the nucleic acid sequence starting from the nucleotide at position 1 and ending with the nucleotide at position 8694 of the nucleic acid sequence set forth in SEQ ID NO:2. The homologous sequence, downstream of the E1A nucleic acid sequence, preferably has a nucleic acid sequence which is homologous with at least 500 contiguous by and more preferably at least 5000 contiguous by of the nucleic acid sequence starting from the nucleotide at position 10580 and ending with the nucleotide at position 18009 of the nucleic acid sequence set forth in SEQ ID NO:2. And, more preferably, said homologous sequence, downstream of the E1A nucleic acid sequence, consists in the nucleic acid sequence starting from the nucleotide at position 10580 and ending with the nucleotide at position 18009 of the nucleic acid sequence set forth in SEQ ID NO:2.

Accordingly, the present invention also relates to an avian cell comprising an E1A nucleic acid sequence characterized in that said cell is obtained by a process comprising the step of transfecting the cell with a non viral vector comprising said E1A nucleic acid sequence, wherein said cell does not comprise an E1B nucleic acid sequence and wherein said E1A nucleic acid sequence is operably linked to the cell's endogenous HPRT promoter.

According to a preferred embodiment, the vector used in the process according to the invention comprises a first selection marker, wherein this first selection marker is a positive selection marker and wherein said first selection marker is surrounded by the homologous sequences comprised in the vector. With this respect, the homologous recombination process which occurs between the vector and the genome of the cell leads to the integration of the E1A nucleic acid sequence and of the first selection marker. When the transfer vector is circular, "surrounded" means that the first selection marker and the E1A nucleic acid sequence are positioned in the same section of the vector, said section being delimited by the homologous sequences.

As used herein, the term positive selection marker notably refers to a gene encoding a product that enables only the cells that carry the gene to survive and/or grow under certain conditions. Typical selection markers encode proteins that confer resistance to antibiotics or other toxins, e.g., ampicillin, neomycin, methotrexate, or tetracycline, complement auxotrophic deficiencies, or supply critical nutrients not available from complex media. In a preferred embodiment according to the invention, the first selection marker encodes a protein that confers resistance to antibiotics.

The integration of the first selection marker allows the selection of the cells that have incorporated the E1A nucleic acid sequence. Accordingly, the process according to the invention can further comprise a step wherein said cells are cultivated in a medium which only allows the growth of the cells which have incorporated the first selection marker. For example, in a medium which comprises an antibiotic.

According to a more preferred embodiment of the invention, the first selection marker, in the vector, is surrounded by sequences allowing its suppression. Said sequences allowing the suppression of the first selection marker do not surround the E1A nucleic acid sequence. When the vector is circular, the sequences allowing the suppression of the first selection marker, the first selection marker and the E1A nucleic acid sequence are positioned in the same section of the transfer vector, said section being delimited by the homologous sequences.

Sequences allowing the suppression of a nucleic acid fragment are well known to the one skilled in the art (Nunes-Duby, S. et al., 26 NUCLEIC ACIDS RES. 391-406 (1998)). These sequences can be recognized by one or more specific enzymes which induce the suppression of the nucleic acid comprised between said sequences, these enzymes are called "recombinase". For example, three well-known recombinases allowing the suppression of a nucleic acid fragment are the FLP, ISCE1, and Cre recombinases.

A typical site-specific recombinase is Cre recombinase. Cre is a 38-kDa product of the cre (cyclization recombination) gene of bacteriophage P1 and is a site-specific DNA recombinase of the Int family. Sternberg, N. et al., 187 J. MOL. BIOL. 197-212 (1986). Cre recognizes a 34-bp site on the P1 genome called loxP (locus of X-over of P1) and efficiently catalyzes reciprocal conservative DNA recombination between pairs of loxP sites. The loxP site consists of two 13-bp inverted repeats flanking an 8-bp nonpalindromic core region. Cre-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phophotyrosine DNA-protein linkage with the enzyme.

Another site-specific recombinase is the I-SceI. Other intron-homing endonuclease, for instance I-TliI, I-CeuI, I-CreI, I-PpoI, and PI-PspI, can also be substituted for I-Scel in the process according to the invention. Many are listed by Belfort and Roberts (25 NUCLEIC ACIDS RESEARCH 3379-3388 (1997)). Many of these endonucleases derive from organelle genomes in which the codon usage differs from the standard nuclear codon usage. To use such genes for nuclear expression of their endonucleases it may be necessary to alter the coding sequence to match that of nuclear genes. I-ScеI is a double-stranded endonuclease that cleaves DNA within its recognition site. I-ScеI generates a 4 bp staggered cut with 3'OH overhangs.

The enzyme I-ScеI has a known recognition site. The recognition site of I-ScеI is a non-symmetrical sequence that extends over 18 bp.

```
                            (SEQ ID NO: 4)
5' TAGGGATAACAGGGTAAT3'

(SEQ ID NO: 5)
3' ATCCCTATTGTCCCATTA5'
```

Another site-specific recombinase is the FLP recombinase. Flp recombinase recognizes a distinct 34-bp minimal site which tolerates only limited degeneracy of its recognition sequence (Jayaram, 1985; Senecoff et al., 1988). The interaction between Flp recombinase and a FRT sequence have been examined (Panigrahi et al., 1992). Examples of variant FRT sequences are given by Jayaram (1985) and Senecoff et al. (1988), and an assay for Flp-mediated recombination on different substrates is described by Snaith et al. (1996).

Accordingly, the process according to the invention can further comprise a step consisting in suppressing the first selection marker from the genome of said primary cell. In order to suppress said first selection marker, the cell is transfected by the gene coding the recombinase specific for the sequences allowing the suppression of the first selection marker. Methods and vector able to transfer said gene into the cell are well known to the one skilled in the art, for example, the method disclosed in Example 4 of the present application can be used. Vectors previously described can also be used.

According to a preferred embodiment, the vector used in the process according to the invention comprises a second selection marker which is not surrounded by said homologous sequences, wherein said second selection marker is a negative selection marker. Said second selection marker is particularly useful when the vector, used in the process according to the invention, is circular. The presence of said second selection marker allows the destruction of the cells in which the homologous recombination process has lead to the introduction of the section of the transfer vector that does not comprise the E1A nucleic acid sequence. When the vector is circular, the fact that the second selection marker is not surrounded by said homologous sequences means that the second selection marker and the E1A nucleic acid sequence are not positioned in the same section of the transfer vector, said section being delimited by the homologous sequences.

Accordingly, the process according to the invention can further comprise a step wherein the cells are cultivated in a medium which only allows the growth of the cells which have not incorporated the second selection marker. Said step can be made simultaneously with or separately from the step wherein said primary cells are cultivated in a medium which only allows the growth of the cells which have incorporated the first selection marker.

According to a preferred embodiment of the invention, the vector comprises a third selection marker wherein said third selection marker is a negative selection marker and wherein said third selection marker is located between the sequences allowing the suppression of the first selection marker. This means that the step consisting in suppressing the first selection marker will also lead to the suppression of the third selection marker. The presence of the third selection marker allows the destruction of the cells in which the first selection marker is present. When the vector is circular, the fact that the third selection marker is located between the sequences allowing the suppression of the first selection marker means that the third selection marker and the first selection marker are positioned in the same section of the transfer vector, said section being delimited by the sequences allowing the suppression of the first selection marker.

As used herein, the term negative selection marker notably refers to a gene encoding a product that kills the cells that carry the gene under certain conditions. These genes notably comprise "suicide gene". The products encoded by these genes are able to transform a prodrug in a cytotoxic compound. Numerous suicide gene/prodrug pairs are currently available. There may be mentioned more particularly the pairs:

herpes simplex virus type I thymidine kinase (HSV-1 TK) and acyclovir or ganciclovir (GCV) (Caruso et al., 90 Proc. Natl. Acad. Sci. USA 7024-7028 (1993); Culver et al., 256 Science 1550-1552 (1992); Ram et al., 3 Nat. Med. 1354-1361 (1997));

cytochrome p450 and cyclophosphamide (Wei et al., 5 Human Gene Therapy 969-978 (1994));

purine nucleoside phosphorylase from *Escherichia coli* (*E. coli*) and 6-methylpurine deoxyribonucleoside (Sorscher et al., 1 Gene Therapy 233-238 (1994));

guanine phosphoribosyl transferase from *E. coli* and 6-thioxanthine (Mzoz and Moolten, 4 Human Gene Therapy 589-595 (1993));

cytosine deaminase (CDase) and 5-fluorocytosine (5FC);

FCU1 and 5-fluoro-cytosine (5FC) (WO 99/54481); and

FCU1-8 and 5-fluoro-cytosine (5FC) (WO 2005/007857).

Said third selection marker allows the selection of the cells in which the suppression of the first selection marker has occurred. Accordingly, the process according to the invention can further comprise a step in which said cell is cultivated in a medium which does not allow the growth of the cell comprising the third selection marker. For example, a medium, which does not allow the growth of the cells comprising FCU1 as a third selection marker, comprises 5-Fluorocytosine.

The first, second, and third selection markers can be used separately. For example, the vector used in the process according to the invention can comprise the first and the third selection markers but not the second one, or the second and the third selection markers but not the first one.

According to a preferred embodiment of the invention, the E1A nucleic acid sequence, the first, the second, and/or the third selection marker are placed under the control of the elements necessary for their expression in the cell to be immortalized.

The elements necessary for the expression consist of the set of elements allowing the transcription of the nucleotide sequence to RNA and the translation of the mRNA to a polypeptide, in particular the promoter sequences and/or regulatory sequences which are effective in said cell, and optionally the sequences required to allow the excretion or the expression at the surface of the target cells for said polypeptide. These elements may be regulatable or constitutive. Of course, the promoter is adapted to the vector selected and to the host cell. There may be mentioned, by way of example, the eukaryotic promoters of the genes PGK (Phospho Glycerate Kinase), MT (metallothionein; McIvor et al., 7 Mol. Cell Biol. 838-848 (1987)), α-1 antitrypsin, CFTR, the promoters of the gene encoding muscle creatine kinase, actin pulmonary surfactant, immunoglobulin or β-actin (Tabin et al., 2 MOL. CELL BIOL. 416-436 (1982)), SRα (Takebe et al., 8 MOL. CELL. 466-472 (1988)), the SV40 virus (Simian Virus) early promoter, the RSV (Rous Sarcoma Virus) LTR, the MPSV promoter, the TK-HSV-1 promoter, the Cytomegalovirus (CMV) early promoter. The CMV early promoter is most particularly preferred.

The present invention more particularly relates, but is not limited to, a process for immortalizing a cell comprising:
  transferring into an avian cell a vector comprising:
    an E1A nucleic acid sequence surrounded by homologous sequences;
    a first selection marker wherein said first selection marker is a positive selection marker and wherein said first selection marker is surrounded by said homologous sequences;
    sequences allowing the suppression of the first selection marker;
    a second selection marker which is not surrounded by said homologous sequences, wherein said selection marker is a negative selection marker; and
    a third selection marker wherein said third selection marker is a negative selection marker and wherein said third selection marker is located between the sequences allowing the suppression of the first selection marker;
  cultivating said cells in a medium which only allows the growth of the cells which have incorporated the first selection marker;
  cultivating said cells in a medium which does not allow the growth of the cells which have incorporated the second selection marker;
  excluding the first selection marker from the genome of said cell; and
  cultivating said cell in a medium which does not allow the growth of the cells comprising the third selection marker.

According to a specific embodiment, the present invention also relates to an immortalized avian cell line comprising a E1A nucleic acid sequence as set forth in SEQ ID NO:1 and a nucleic acid sequence coding a recombinant telomerase reverse transcriptase as set forth in SEQ ID NO:3, selected in the group consisting of:
  an immortalized avian cell line deposited at the European Collection of Cell Cultures (ECACC) under accession number 09070701,
  an immortalized avian cell line deposited at the ECACC under accession number 09070702,
  an immortalized avian cell line deposited at the ECACC under accession number 09070703, and
  derivatives thereof.

Derivatives of the deposited *Cairina moschata* immortalized avian cell lines of the invention refer to *Cairina moschata* immortalized avian cell lines derived from the deposited ones by, for example:
  subcloning of the said deposited *Cairina moschata* immortalized avian cell line (ECACC 09070701, ECACC 09070702 or ECACC 09070703);
  adaptation of the said deposited *Cairina moschata* immortalized avian cell line (ECACC 09070701, ECACC 09070702 or ECACC 09070703) to a specific culture medium (e.g., medium allowing the growth of the cell line in suspension) and/or to specific culture conditions (e.g., temperature; % $CO_2$);
  deletion or mutation of one or more genes of *Cairina moschata* involved in saccharide fucose modification (HARUE IMAI-NISHIYA et al., BMC BIOTECHNOLOGY (2007)) in order to produced non-fucosylated proteins, and more particularly non-fucosylated antibodies.

According to a preferred embodiment, said derivatives of the deposited *Cairina moschata* immortalized avian cell line are obtained by deletion or mutation of α1,6-fucosyltransferase (FUT8) and/or GDP-mannose 4,6-dehydratase (GMD) genes;
  deletion or mutation of one or more genes of *Cairina moschata* involved in interferon resistance in order to reduce the immune response of the cell line. According to a preferred embodiment, said derivatives of the deposited *Cairina moschata* immortalized avian cell line are obtained by deletion or mutation of gene(s) selected in the group consisting of STAT1 gene, STAT2 gene, STAT3 gene and STAT5 gene;
  overexpression of one or more *Cairina moschata*'s anti-apoptotic gene(s), or transformation with one or more exogenous anti-apoptotic gene(s) in order to render the cell line more resistant to the culture conditions, in particular for maintaining confluence. According to a preferred embodiment, said anti-apoptotic gene(s) is/are selected in the group consisting of p19E1B human adenovirus gene, bcl-2 gene, mcl-1 gene, Bcl-xL gene, Bcl-w gene, a1 gene, ICP34.5 herpes simplex virus gene, and p35 baculovirus gene;
  overexpression of one or more *Cairina moschata*'s genes involved in controlling the cell cycle using vectors which are suitable for increasing the rate of proliferation. According to a preferred embodiment, said gene(s) involved in controlling the cell cycle, is/are selected in the group consisting of p53 gene, p21 gene, p27 gene, and p57 gene;
  modifying the viral sensitivity spectrum of the cell line by transformation with one or more genes which encode receptors for the viruses of interest, with a view to multiplying these viruses. According to a preferred embodiment, said gene(s) which encode receptors for the viruses of interest, is/are gene(s) which encode measles virus CD46 receptor.

The cell according to the invention can further comprise one or more nucleic acid sequence(s) allowing the propagation of a defective virus. "Defective virus" refers to a virus in which one or more viral gene necessary for its replication are deleted or rendered nonfunctional. The term "nucleic acid sequence allowing the propagation of a defective virus" refers to a nucleic acid sequence supplying in trans the function(s) which allows the replication of the defective virus. In other words, said nucleic acid sequence(s) code(s) the proteins(s) necessary for the replication and encapsidation of said defective virus.

The cell according to the invention can also comprise a nucleic acid sequence coding a substance of interest. As used herein, a substance of interest may include, but is not limited to, a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-α, interferon-β, interferon-γ, blood clotting factors, for example, Factor VIII, Factor IX, or tPA or combinations thereof. "Substance of interest" also refers to industrial enzymes, for example for use within pulp and paper, textile modification, or ethanol production. Finally, "substance of interest" also refers to protein supplement or a value-added product for animal feed.

According to a preferred embodiment of the invention, the cell according to the invention also comprises a nucleic acid sequence coding a recombinant telomerase reverse transcriptase and more preferably, the recombinant telomerase reverse transcriptase described in EP-06360047.2. In a preferred embodiment of the invention described in EP-06360047.2, nucleic acid sequence coding the recombinant telomerase reverse transcriptase has at least 70%, more preferably at least 90%, and more preferably at least 95% nucleic acid sequence identity to the nucleic acid sequence set forth in SEQ ID NO:2 of EP-06360047.2. Preferred nucleic acid sequence coding the recombinant telomerase reverse transcriptase described in EP-06360047.2 is as set forth in SEQ ID NO:2 of EP-06360047.2. Telomerase reverse transcriptase nucleic acid sequence SEQ ID NO:2 described in EP-06360047.2 corresponds to telomerase reverse transcriptase nucleic acid sequence SEQ ID NO:3 in the present invention. As a consequence, according to a preferred embodiment of the invention, the cell according to the invention also comprises a nucleic acid sequence coding a recombinant telomerase reverse transcriptase and more preferably a nucleic acid sequence coding a recombinant telomerase reverse transcriptase having at least 70%, more preferably at least 90%, and more preferably at least 95% nucleic acid sequence identity to SEQ ID NO:3. More preferably, nucleic acid sequence coding a recombinant telomerase reverse transcriptase is as set forth in SEQ ID NO:3 (dTERT).

The cells obtained by the process according to the invention, the cell of the invention and the cells derived thereof are notably useful for the replication of a virus. Said viruses can be live, attenuated, recombinant, or not. More preferably, said cells are particularly useful for the replication of poxvirus (vaccinia virus, in particular MVA, canarypoxvirus, etc.), an adenovirus, a retrovirus, an herpesvirus, an alphavirus, a foamy virus, or from an adenovirus-associated virus.

Retroviruses have the property of infecting, and in most cases integrating into, dividing cells and in this regard are particularly appropriate for use in relation to cancer. A recombinant retrovirus generally contains the LTR sequences, an encapsidation region and the nucleotide sequence according to the invention, which is placed under the control of the retroviral LTR or of an internal promoter such as those described below. A retroviral vector may contain modifications, in particular in the LTRs (replacement of the promoter region with a eukaryotic promoter) or the encapsidation region (replacement with a heterologous encapsidation region, for example the VL30 type) (see FR-9408300 and FR-9705203).

An adenoviral vector can lack all or part of at least one region which is essential for replication and which is selected from the E1, E2, E4, and L1 L5 regions. A deletion of the E1 region is preferred. However, it can be combined with (an) other modification(s)/deletion(s) affecting, in particular, all or part of the E2, E4, and/or L1 L5 regions. By way of illustration, deletion of the major part of the E1 region and of the E4 transcription unit is very particularly advantageous. For the purpose of increasing the cloning capacities, the adenoviral vector can additionally lack all or part of the non-essential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, e.g., Graham and Prevect, 7 METHODS IN MOLECULAR BIOLOGY 109-128; Ed: E. J. Murey, The Human Press Inc (1991)).

Poxvirus family comprises viruses of the Chordopoxvirus and Entomopoxvirus subfamilies. Among these, the poxvirus according to the invention is preferably chosen from the group comprising Orthopoxviruses, Parapoxviruses, Avipoxviruses, Capripoxviruses, Leporipoxviruses, Suipoxviruses, Molluscipoxviruses, and Yatapoxviruses. According to a more preferred embodiment, the poxvirus of the invention is an orthopoxvirus.

The Orthopoxvirus is preferably a vaccinia virus and more preferably a modified vaccinia virus Ankara (MVA), in particular MVA 575 (ECACC V00120707) and MVA-BN (ECACC V00083008).

The term "recombinant virus" refers to a virus comprising an exogenous sequence inserted in its genome. As used herein, an exogenous sequence refers to a nucleic acid which is not naturally present in the parent virus.

In one embodiment, the exogenous sequence encodes a molecule having a directly or indirectly cytotoxic function. By "directly or indirectly" cytotoxic is meant that the molecule encoded by the exogenous sequence may itself be toxic (for example, ricin, tumor necrosis factor, interleukin-2, interferon-gamma, ribonuclease, deoxyribonuclease, *Pseudomonas* exotoxin A) or it may be metabolised to form a toxic product, or it may act on something else to form a toxic product. The sequence of ricin cDNA is disclosed in Lamb et al. (148 EUR. J. BIOCHEM. 265-270 (1985)) incorporated herein by reference.

In a preferred embodiment of the invention, the exogenous sequence is a suicide gene. A suicide gene encodes a protein able to convert a relatively non-toxic prodrug to a toxic drug. For example, the enzyme cytosine deaminase converts 5-fluorocytosine (5FC) to 5-fluorouracil (5FU) (Mullen et al. 89 PNAS 33 (1992)); the herpes simplex enzyme thymidine kinase sensitises cells to treatment with the antiviral agent ganciclovir (GCV) or aciclovir (Moolten, 46 CANCER RES. 5276 (1986); Ezzedine et al., 3 NEW BIOL 608 (1991)). The cytosine deaminase of any organism, for example *E. coli* or *Saccharomyces cerevisiae*, may be used.

Thus, in a more preferred embodiment of the invention, the gene encodes a protein having a cytosine deaminase activity and even more preferably a protein as described in WO 2005/007857 and WO 99/54481.

In a further embodiment the exogenous gene encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a still further embodiment the exogenous gene encodes an antisense RNA.

By "antisense RNA" we mean an RNA molecule which hybridises to, and interferes with the expression from a mRNA molecule encoding a protein or to another RNA molecule within the cell such as pre-mRNA or tRNA or rRNA, or hybridises to, and interferes with the expression from a gene.

In another embodiment of the invention, the exogenous sequence replaces the function of a defective gene in a target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumor-suppressor genes that have undergone mutation.

Examples of protooncogenes are ras, src, bcl and so on; examples of tumor-suppressor genes are p53 and Rb.

In a further embodiment of the invention, the exogenous sequence encodes a Tumor Associated Antigen (TAA). TAA refers to a molecule that is detected at a higher frequency or density in tumor cells than in non-tumor cells of the same tissue type. Examples of TAA include, but are not limited to, CEA, MART-1, MAGE-1, MAGE-3, GP-100, MUC-1, MUC-2, pointed mutated ras oncogene, normal or point mutated p53, overexpressed p53, CA-125, PSA, C-erb/B2, BRCA I, BRCA II, PSMA, tyrosinase, TRP-1, TRP-2, NY-ESO-1, TAG72, KSA, HER-2/neu, bcr-abl, pax3-fkhr, ews-fli-1, surviving, and LRP. According to a more preferred embodiment the TAA is MUC1.

The recombinant virus can comprise more than one exogenous sequence and each exogenous sequence can encodes more than one molecule. For example, it can be useful to associate in a same recombinant poxvirus, an exogenous sequenced coding a TAA with an exogenous sequence coding a cytokine.

In another embodiment of the invention, the exogenous gene encodes an antigen. As used herein, "antigen" refers to a ligand that can be bound by an antibody; an antigen need not itself be immunogenic.

Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus (preferentially non structural protein from genotype 1b strain ja) and hepatitis E virus, or from other viral pathogens, such as Respiratory Syncytial Virus, Human Papilloma Virus (preferentially the E6 and E7 protein from the HPV16 strain) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Establishment of an Immortalized Avian Cell Line Comprising an E1A Nucleic Acid Sequence A. Plasmid Constructs A-1. Plasmid Constructs for Random Insertion.

A plasmid sharing no specific sequence of homology with the *Cairina moschata* genome (plasmid E1A) has been used for this purpose (FIG. 1).

A-2. Plasmid Constructs for Targeted Insertion.

A plasmid comprising two 5 kb fragments homologous to the *Cairina moschata* HPRT gene surrounding the E1A nucleic acid sequence (SEQ ID No:1) and two selection markers has been constructed. The HPRT gene encoding for the hypoxanthine guanine phosphoryl transferase has been selected as an adequate site for the constitutive expression of the E1A nucleic acid sequence.

These two selection marker are the FCU1 gene (Erbs et al. Cancer Res. 2000. 15. 60.:3813-22) under the control of a CMV promoter (Thomsen et al. P.N.A.S. 1984. 81. 3:659-63) and the Neomycin (or Puromycin) resistance gene placed under the control of a SV40 promoter. Neomycin (or Puromycin) resistance and FCU-1 expression cassette are surrounded by Sce1 cleavage sites that allow the elimination of the selection cassettes from the final cell line. Outside of the HPRT gene arms is inserted a selection marker coding the HSVTK driven by an RSV promoter (FIG. 2).

B. Preparation of CEC Batch from *Cairina moschata* Eggs and Subpopulations Description B.1 Preparation of CEC Batch from 12 Old *Cairina moschata* Eggs and Subpopulations Description.

25 fertilized SPF eggs are incubated at 37.5° C. Eggs are opened after 12 days incubation following available protocol.

23 embryos are minced, washed once in Phosphate Buffered Saline-Dulbecco (PBS) and dissociated in TrypLE Select (Invitrogen) 5 hours at room temperature.

After low speed centrifugation cells are resuspended in Basal Medium Eagle (MBE) supplemented with 10% fetal calf serum (FCS), gentamycine 0.04 g/L, seeded in 500 cm$^2$ triple flasks and incubated at 37° C. 5% $CO_2$.

After 24 h the confluent cells are removed from the flasks using TrypLE Select (5 mL/triple flask), part of the cells were reseeded in 175 cm$^2$ flasks for second passage. The remaining cells were concentrated at 10$^7$ cell/mL in appropriate media (60% BME, 30% FCS and 10% DMSO) and frozen in a isopropyl alcool regulated container (NALGENE® "Mr. Frosty" 1° C. freezing. Container) at −80° C. prior to transfer in liquid azote for long term storage, constituting the initial cell bank (50×1.5·10$^7$ cells/vial, 44×1·10$^7$ cells/vial).

Cells remained in culture are passaged classically up to 18 passages, during the 3 first passages non attached cells are collected by low centrifuging the conditioned media, reseeded and further passaged in the same way as the initial culture.

Subpopulations, displaying characteristic different morphological features, have been reproducibly isolated during the culture's lifespan.

B.2. Preparation of CEC Batch from 19 Old *Cairina moschata* Eggs and Subpopulations Description.

29 fertilized SPF *Cairina Moschata* eggs obtained from AFFSSA Ploufragan are incubated at 37.5° C. in humid atmosphere.

Eggs are opened after 19 days and embryos sterilely extracted. 20 embryos are beheaded, limbs removed as well as the liver used for other cell preparation. The embryonic torsi are minced, washed once in PBS Dulbecco (Sigma, Réf. D8537, Lot 46K2428) and dissociated in 500 mL TrypLE Select (Gibco, Réf. 12563, Lots 1319986 and 1339844) 2 hours at 37° C.

After 5 minutes 2000 rpm centrifugation cells are resuspended in BME (Basal Medium Eagle, Gibco, Réf. 41010, Lot 8270) supplemented with 10% fetal calf serum (JRH, Réf. 12003-1000M, Lot. 5A0102, Code TG P4001Q), gentamycin 0.04 g/L and L-Glutamine 4 mM. A final volume of 1.5 L (1.9·10$^6$ cell/mL) suspension is seeded in 10 triple flasks (500 cm$^2$) and incubated at 37° C. 5% $CO_2$.

After 24 h the confluent cells are washed with PBS and removed from the flasks using TrypLE Select. Cells are counted and centrifuged 4-5 minutes at 2,000 rpm. The pellet is concentrated at 5·10$^6$ or 10$^7$ cell/mL in appropriate media (60% BME, 30% FCS and 10% DMSO). The suspension is filled in cryovials (Nunc) and frozen at −80° C. with a meanwhile 2 h step at −20° C., prior to transfer in liquid nitrogen for long term storage, constituting the primary cell bank (110 cryovials, $10^7$ cells/vial) of CETC19p1 (Duck Torso Embryonic Cells, 19 days old embryos, passage 1).

In a preferred embodiment of the present invention, the preparation of CEC batch from *Cairina moschata* eggs is performed according to alternative B.2. (from 19 old *Cairina moschata* eggs).

C. Methods of Transfection

A large number of transfection methods are known in the art to introduce a vector capable of directing expression of a nucleotide sequence of interest. A non limiting list of these methods is listed hereafter: $CaPO_4$ precipitation, electroporation, lipofectin transfection method. A given example is based on $CaPO_4$ precipitation procedure.

Cells should be around 80-50% confluency. The medium is change two hours before $CaPO_4$/DNA addition. The 30 μg DNA is resuspended in 31 μl 2M $CaCl_2$—161.3 mM Tris pH 7.6. $H_2O$ is added to a final volume of 0.5 ml.

Then, 2 alternatives:

a) Per transfection, 0.5 ml of 2×HEBS is distributed in 15 ml sterile Falcon tube and the DNA solution is added drop wise while gently vortexing or bubbling the DNA solution in. The solution should become milky. The mix is let stand at room temperature for 10-30 min. Then pipette in and out once with sterile pipette in tissue culture cabinet to break up flakes and apply drop wise to cells. Cells are then incubated between 6 hours to overnight at 37° C. A fine precipitate should cover the cell surface. In order to complete the transfection procedure warm up to 37° C. the glycerol shock solution. The medium is aspirate off, 5 ml BME is added to wash the cell layer, the medium is then aspirate off and 1 ml glycerol shock solution is added for 2 min or less. Subsequently 10 ml BME are added gently to dilute the glycerol and BME-glycerol is completely removed. 10 ml of desired medium is then added and plates are incubated at the appropriate temperature.

or b) Per transfection, 0.5 ml of 2×HEBS is distributed in 15 ml sterile Falcon tube and the DNA solution is added drop wise while gently vortexing or bubbling the DNA solution in. The solution should become milky. The mix is let stand at room temperature for 10-30 min. Then pipette in and out once with sterile pipette in tissue culture cabinet to break up flakes and apply drop wise to cells. A fine precipitate should cover the cell surface. Cells are then incubated between 6 hours to overnight at 37° C.

In a preferred embodiment of the present invention, the transfection ($CaPO_4$ precipitation) is performed according to alternative b).

D. Methods of Selection

D-1. Method of Selection for Random Insertion:

Selection pressure is applied 48 to 72 hours after transfection: cells are dissociated with TrypLE select, low speed centrifuged and reseeded in BME with FCS 10% and G418 800 μg/mL, preferably 500 μg/mL (and optionally Ganciclovir 25 μg/mL, preferably 10 μg/mL).

Cells are serially passaged until individual growing clones can be isolated.

D-2. Method of Selection for Targeted Insertion:

Selection pressure is applied 48 to 72 hours after transfection: cells are dissociated with TrypLE select, low speed centrifuged and reseeded in BME with FCS 10%; Ganciclovir 25 μg/mL, preferably 10 μg/mL; and G418 800 μg/mL, preferably 500 μg/mL (or Puromycin 0.5 μg/mL).

Cells are serially passaged until individual growing clones can be isolated.

Cell clones are subsequently transfected with a meganuclease I-SceI expression plasmid following the method described below.

To select the elimination of the selection markers 5-Fluorocytosine (5-FC) is applied 48 hours after transfection: cells are dissociated with TrypLE select, low speed centrifuged and reseeded in media with 5-FC concentration ranging from $10^{-3}$ to $10^{-7}$ M and maintained G418 (or Puromycin)/Ganciclovir selection (BME with FCS 10%; 5-FC Ganciclovir 25 μg/mL, preferably 10 μg/mL; and G418 800 μg/mL, preferably 500 μg/mL (or Puromycin 0.5 μg/mL) (FIG. 3).

Example 2

Establishment of an Immortalized Avian Cell Line Comprising an E1A Nucleic Acid Sequence and a Recombinant Telomerase Reverse Transcriptase Nucleic Acid Sequence A. Plasmid Constructs A-1. Plasmid Constructs for Random Insertion.

A plasmid sharing no specific sequence of homology with the *Cairina moschata* genome has been used for this purpose.

A-2. Plasmid Constructs for Targeted Insertion.

A plasmid (plasmid dTERT-E1A) comprising two 5 kb fragments homologous to the *Cairina moschata* HPRT gene surrounding the *Cairina moschata* telomerase reverse transcriptase gene (SEQ ID NO:3), the E1A nucleic acid sequence (SEQ ID NO:1) and two selection markers has been constructed. The HPRT gene encoding for the hypoxanthine guanine phosphoryl transferase has been selected as an adequate site for the constitutive expression of the E1A nucleic acid sequence.

These two selection marker are the FCU1 gene (Erbs et al. Cancer Res. 2000. 15. 60.:3813-22) under the control of a CMV promoter (Thomsen et al. P.N.A.S. 1984. 81. 3:659-63) and the Puromycin resistance gene placed under the control of a SV40 promoter. Puromycin resistance and FCU-1 expression cassette are surrounded by SceI cleavage sites that allow the elimination of the selection cassettes from the final cell line. Outside of the HPRT gene arms is inserted a selection marker coding the HSVTK driven by an RSV promoter (FIG. 4).

B. Preparation of CEC Batch from 19 Old *Cairina moschata* Eggs and Subpopulations Description 29 fertilized SPF *Cairina Moschata* eggs obtained from AFFSSA Ploufragan are incubated at 37.5° C. in humid atmosphere.

Eggs are opened after 19 days and embryos sterilely extracted. 20 embryos are beheaded, limbs removed as well as the liver used for other cell preparation. The embryonic torsi are minced, washed once in PBS Dulbecco (Sigma, Réf. D8537, Lot 46K2428) and dissociated in 500 mL TrypLE Select (Gibco, Réf. 12563, Lots 1319986 and 1339844) 2 hours at 37° C.

After 5 minutes 2000 rpm centrifugation cells are resuspended in BME (Basal Medium Eagle, Gibco, Réf. 41010, Lot 8270) supplemented with 10% fetal calf serum (JRH, Réf. 12003-1000M, Lot. 5A0102, Code TG P4001Q), gentamycin 0.04 g/L and L-Glutamine 4 mM. A final volume of 1.5 L ($1.9 \cdot 10^6$ cell/mL) suspension is seeded in 10 triple flasks (500 cm²) and incubated at 37° C. 5% $CO_2$.

After 24 h the confluent cells are washed with PBS and removed from the flasks using TrypLE Select. Cells are counted and centrifuged 4-5 minutes at 2000 rpm. The pellet is concentrated at $5 \cdot 10^6$ or $10^7$ cell/mL in appropriate media (60% BME, 30% FCS and 10% DMSO). The suspension is filled in cryovials (Nunc) and frozen at −80° C. with a meanwhile 2 h step at −20° C., prior to transfer in liquid nitrogen for long term storage, constituting the primary cell bank (110 cryovials, $10^7$ cells/vial) of CETC19p1 (Duck Torso Embryonic Cells, 19 days old embryos, passage 1).

C. Methods of Transfection

A large number of transfection methods are known in the art to introduce a vector capable of directing expression of a nucleotide sequence of interest. A non limiting list of these methods is listed hereafter: $CaPO_4$ precipitation, electroporation, lipofectin transfection method. A given example is based on electroporation.

Transfection is performed using Amaxa's Nucleofector device and the Basic Fibroblast kit (Amaxa, Cat N° VPI-1002). Cells are centrifuged 10 min at 700 rpm (100 g) and resuspended in Basic Nucleofector Solution (100 µL per $10^6$ cells); 100 µL suspension are mixed with 3 to 6 µg DNA and transferred to a cuvette placed in the Nucleofector (U-12 program). After electroporation the sample is transferred to a 6 cm culture dish, filled with 5 mL culture media, preequilibrated in the 37° C./5% $CO_2$ incubator. After incubation over night at 37° C. 5% $CO_2$ culture media is renewed and incubation pursued.

D. Methods of Selection

D-1. Method of Selection for Random Insertion:

Selection pressure is applied 48 to 72 hours after transfection: cells are dissociated with TrypLE select, low speed centrifuged and reseeded in BME with FCS 10%, Ganciclovir 25 µg/mL, preferably 10 µg/mL; and G418 800 µg/mL, preferably 500 µg/mL.

Cells are serially passaged until individual growing clones can be isolated.

D-2. Method of Selection for Targeted Insertion:

Selection pressure is applied 48 to 72 hours after transfection: cells are dissociated with TrypLE select, low speed centrifuged and reseeded in BME with FCS 10%; Ganciclovir 25 µg/mL, preferably 10 µg/mL; and Puromycin 0.5 µg/mL.

Cells are serially passaged until individual growing clones can be isolated.

Cell clones are subsequently transfected with a meganuclease I-SceI expression plasmid following the method described below.

To select the elimination of the selection markers 5-Fluorocytosine (5-FC) is applied 48 hours after transfection: cells are dissociated with TrypLE select, low speed centrifuged and reseeded in media with 5-FC concentration ranging from $10^{-3}$ to $10^{-7}$ M and maintained Puromycin/Ganciclovir selection (BME with FCS 10%; 5-FC Ganciclovir 25 µg/mL, preferably 10 µg/mL; and Puromycin 0.5 µg/mL).

Example 3

ECACC 09070701, ECACC 09070702, and ECACC 09070703 Immortalized *Cairina moschata* Cell Lines The *Cairina moschata* cell lines ECACC 09070701 (T17-17703B), ECACC 09070702 (T17-17703B2), and ECACC 09070703 (T17-17703A) were obtained from primary embryonic *Cairina moschata* cells as described in Example 2 by target insertion (electroporation) with the plasmid dTERT-E1A.

The cells lines arose between 210 and 260 days post-transfection, after a senescence/crisis phase, as the subpopulations ECACC 09070701, ECACC 09070702, and ECACC 09070703 entered a new continuous exponential growth phase. Corresponding growth curves (FIG. 8) show the populations' evolution until 456 days post-transfection. The numbers of population doublings (PDL) calculated for this period (ECACC 09070703: 138 PDL; ECACC 09070701: 131 PDL; ECACC 09070702: 166 PDL) are far beyond the Hayflick limit. The *Cairina moschata* cell lines ECACC 09070701 (T17-17703B), ECACC 09070702 (T17-17703B2), and ECACC 09070703 (T17-17703A) are consequently referred as immortalized cell lines.

The three *Cairina moschata* cell lines are distinct cell lines which display different morphologies: The *Cairina moschata* ECACC 09070703 cells have an epithelial like morphology (FIG. 7), whereas the *Cairina moschata* ECACC 09070701 and ECACC 09070702 cells form syncitia like layers (respectively FIG. 5 and FIG. 6). The cells of the three cell lines are small cells, growing in a stable static monolayer.

The three *Cairina moschata* cell lines also display different generation times: Average population doubling time (PDT) is 30 hours for ECACC 09070702, 35 hours for ECACC 09070701 and 47 hours for ECACC 09070703 (FIG. 9).

The cells of the three cell lines were tested negative for mycoplasma and microbial contaminations.

The population doubling level (PDL) refers to the number of cell generations (biomass 2 fold increase). PDL calculation: PDL=Ln(final/initial cell number)/Ln(2);

The population doubling time (PDT), also called generation time, is the time needed for one population doubling. PDT calculation: PDT=Δt*Ln(2)/Ln(final/initial cell number).

Example 4

Production of Modified Vaccinia Virus Ankara (MVA)

MVA amplification capacities of *Cairina moschata* immortalized avian cell lines ECACC 09070701, ECACC 09070702, and ECACC 09070703 were evaluated and compared to primary chicken embryo fibroblasts (CEFs) usually used as substrate for MVA production. An MVA (Collection Nationale de Cultures de Microorganismes (CNCM) under depositary N602 I-721) expressing eGFP was chosen in order to facilitate virus propagation follow up and titration. *Cairina moschata* immortalized avian cell lines ECACC 09070701, ECACC 09070702, ECACC 09070703 and CEFs were seeded at $2 \cdot 10^6$ cells in T-flask of 25 cm² and cultivated for 24 hours in humid atmosphere at 37° C., 5% $CO_2$. The culture medium (Basal Medium Eagle (BME) supplemented with 10% Foetal Calf Serum (FCS) and 4 mM L-Glutamine) was then removed and cells infected at MOI 0.05 with 500 µL MVA virus diluted in PBS 1% cations, 1% FCS. After a 30 minutes adsorption step, remaining virus suspension was removed, cells washed once with PBS and 5 mL BME 10% FCS were then added to each flask. Fresh culture medium was added and cells replaced in the incubator. Virus was recovered by a freezing-thawing step from cells and supernatant after 0, 24, 48, 72 and 96 hours infection at 37° C., 5% $CO_2$. Recovered virus suspensions were sonicated prior to titration in order to avoid aggregates. Titrations were performed in triplicates on CEFs seeded in 6 cm culture dishes, infected with logarithmic virus dilutions and overlaid with agar. Plaque forming units of MVA, expressing eGFP, were visualized with fluorescent binocular and counted after 72 hours.

Results: As depicted in FIG. 10, the *Cairina moschata* immortalized avian cell lines ECACC 09070701, ECACC 09070702, and ECACC 09070703 were permissive to MVA and enabled MVA amplification comparable to the one obtained with classical CEF substrate. For all the tested avian cell lines, the maximal viral yield was reached 72 h post-infection and was ranging from $2.3 \cdot 10^7$ to $5.7 \cdot 10^7$ total pfu. Concordantly, clear cytopathic effect was observed in all cells (data not shown).

Each patent, patent application, publication, text, and literature article/report cited or indicated herein is hereby expressly incorporated by reference in its entirety for all purposes.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for replicating a virus, wherein said method comprises infecting an immortalized avian cell line as deposited at the European Collection of Cell Cultures (ECACC) under accession number 09070701, accession number 09070702, or accession number 09070703, and those which develop from, differentiate from, or have an ancestor cell therein with said virus, culturing the infected immortalized avian cell line, and recovering said virus from the cell culture.

2. The method according to claim 1, wherein said virus is a live virus, an attenuated virus, or a recombinant virus.

3. The method according to claim 1, wherein said virus is chosen from the group consisting of poxvirus, adenovirus, retrovirus, herpervirus, alphavirus, foamy virus, and adenovirus-associated virus.

4. The method according to claim 1, wherein said virus is a poxvirus.

5. The method according to claim 1, wherein said virus is a vaccinia virus.

6. The method according to claim 1, wherein said virus is a modified vaccinia virus Ankara (MVA).

* * * * *

SEQUENCE LISTING

```
<160> NUMBER OF SEQ ID NOS: 5

<210> SEQ ID NO 1
<211> LENGTH: 1027
<212> TYPE: DNA
<213> ORGANISM: Adenovirus

<400> SEQUENCE: 1
ccgggactga aaatgagaca tattatctgc cacggaggtg ttattaccga agaaatggcc      60
gccagtcttt tggaccagct gatcgaagag gtactggctg ataatcttcc acctcctagc     120
cattttgaac cacctaccct tcacgaactg tatgatttag acgtgacggc ccccgaagat     180
cccaacgagg aggcggtttc gcagattttt cccgactctg taatgttggc ggtgcaggaa     240
gggattgact tactcacttt tccgccggcg cccggttctc cggagccgcc tcacctttcc     300
cggcagcccg agcagccgga gcagagagcc ttgggtccgg tttctatgcc aaaccttgta     360
ccggaggtga tcgatcttac ctgccacgag gctggctttc cacccagtga cgacgaggat     420
gaagagggtg aggagtttgt gttagattat gtggagcacc ccgggcacgg ttgcaggtct     480
tgtcattatc accggaggaa tacgggggac ccagatatta tgtgttcgct ttgctatatg     540
aggacctgtg gcatgtttgt ctacagtaag tgaaaattat gggcagtggg tgatagagtg     600
gtgggtttgg tgtggtaatt ttttttttaa tttttacagt tttgtggttt aaagaatttt     660
gtattgtgat ttttttaaaa ggtcctgtgt ctgaacctga gcctgagccc gagcagaacc     720
ggagcctgca agacctaccc gccgtcctaa aatggcgcct gctatcctga gacgcccgac     780
atcacctgtg tctagagaat gcaatagtag tacggatagc tgtgactccg gtccttctaa     840
cacacctcct gagatacacc cggtggtccc gctgtgcccc attaaaccag ttgccgtgag     900
agttggtggg cgtcgccagg ctgtggaatg tatcgaggac ttgcttaacg agcctgggca     960
acctttggac ttgagctgta aacgcccccag gccataaggt gtaaacctgt gattgcgtgt    1020
gtggtta                                                              1027

<210> SEQ ID NO 2
<211> LENGTH: 26916
<212> TYPE: DNA
<213> ORGANISM: Cairina moschata

<400> SEQUENCE: 2
gctatcactc catttcaagg aagggcaaaa ggccggttca ataccaacat ctgtgtagct      60
aagtaggatg aaatagatta ggtgaccaaa atatctgctt attcagcagg tgttgatcca     120
caggaggttc tacgataaag ctccagtagg agttgtacca gcgtaattcc tggagggcag     180
caataagtcc accatctaca ctccacaaag tctgatcttt aggtacaaag agctgtgctg     240
atctagaatg atgtggttag actgaatctg gctctaaatt tctgttatta gagtattatg     300
tattattaag taagaggcct tgcttcttac tgctgcctaa atgaagatta actttacagt     360
```

```
gaagcagagt gagagatgaa ggggtgataa tgtgtttgaa atatcagact taatctggca    420
ggtgataatc agttcattcc aaaaacgtta atgtgctgaa tcagattgac aagaaaatga    480
atcctaatta gttgaaatta atctgaagag aactgaaagt acatcatagc aaatagtaac    540
tcttcttcca catcacaagg aacagattcc actgtgttag tgatggaggt ttatacaaaa    600
aaaaaaaaaa aagaaaaacc agaacagctc ttaatttata tacttattga agcagattct    660
atatatgcat atgtatgcac attcattaat cagcagtaca tctcaaccct taaaagatcc    720
tggagaactg ttgcttgtca aaaagcactc aggttaggct aacatttgca gcttttgctc    780
tagcatacat ttacattagg tgtaaagaca aggaatgtgt aaaagagggt aaatgcattc    840
ctatctacaa tgttatgtat attttgttcc tgttatattg gctttacttc caaagttgta    900
gtttgcagta ttagtttctt tttattggta tccttgcata tatatatatt caataaatga    960
gttatgaatt tcatatttgc atatctgtcc ttttctgaa agtagaactt taaaactgac     1020
acttcagtgc ataaaagcag tgttccctat tgatgttaaa gtacctcgaa agttttacca    1080
gaagacaagt gagtgcatac ttaaagtatg ctacttactt ggtggtaact gcgtatttgt    1140
gcattgttcc tgactttgtg taatgggtaa gttgctttgt atttaccact tgctaataat    1200
gtgaagtggc tggctcacta aaggttgcca ttctcacctt tcaaggactt cttgaaggct    1260
gtgtcataat aatttagagt aagacagata ctgagagcgc agagtgtaat atagttatgt    1320
tgcagaagag cggatagaca caggatgcat gttagaacca tataaatgtg gtgtaaaaga    1380
tcagcaaaac gaagaattgc ttggaagatg cttggttttg tccaaataaa tagctgctga    1440
gagtgagaga gtgagtgagt aatattcagt attttaaag tgtcgagaaa tgtaatgggg     1500
aaaaatttaa aataaatgtt ttttgtttgt tttaaaagga gctgtgtgct tttatgttga    1560
catgttgatt taattactgc ggtaggtatt tactgtgccc tgggaaacgg tatccccagt    1620
caacacagac ttatttgtca ggaaaaaaat tgtcatagat catcttcaaa taagagttga    1680
caaataatca aatcttgatg gagtataatt attaatactg tgattacata ccatctttg     1740 caagggtttc ctgaaaaggt cagttttaag tcttctattg tcaaatctga tgtttggagt    1800
agttcgctac atggtgtttg atgccatgta aatagttacc agatagacgt tttattttat    1860
gtgctgtatg ttttttgttt tcattcagtc agctggaatc attgaaacag agaaggtttc    1920
tcaagaaata tcctgaacct gttttgtgga tgtcttcatt gcaatagctg gtcactgaaa    1980
tcttggaata acgacagagg aatccatagg cacaggacca aacacctttc attgtcctca    2040
tatagcgtga tgttagggca gagtggtgag tacttcagtg gctcctgtgt ccatgcttta    2100
atgaactcta cttaatctac catatgtaag agacttgcag cacaggcaaa acaagggaag    2160
ttatctttgt gcctagataa tgtaccacat atggtaaaca attttcaagc tcagagaca    2220 aaagaaggat gctgtaaagt ctcaagtctc agcttgtgtc tctgtttcca cctttctgtt    2280
ctttctgttc agacctctgg gccagtaatt taaactggaa aattaatgga acagagaaac    2340
tgtttgtgag cctatagaaa gatcaaattg tgtcagagta atgttgctcc ttctacaccc    2400
agataaactt tttgagcaga ggagaagcag tgaacagagc tttactttca tgactttgca    2460
taagaaaaca tgggaatgtg gtccgagacc aatttaaaaa tagaggtttt gaaaacttgt    2520
ttggaaaaca aaacttgctt ggaaaacccct attcagagct gtgaatcatt cacagacaac   2580
ctcttagggt tgtagccact catcagctga atatgattca acgatatgct gaaaaaaaaa    2640
aacacaaaca ttgttgtgga atgtatgaac aggaatgtag tctgtaagat gcgtgtcttg    2700
gtccttcttc tttaggtaat agtagaacac ctttctggga aaatggtatc cagctgttgt    2760
```

```
aggcactgca ctccatggaa aatgtgaaga aagtggaaat aatccagaga aaagcaatga   2820
gagggatgac aggataaaaa atgagccttg ctttaaggtg atgagagaaa agtgttttc    2880 aaatctgtaa gagagccaca gagaagaaag aaagaaacag ttctcatcat tgcaggtagg   2940
acaagaaaaa taggtttaag ttgctgcagg aagcctttag cttagacatc agaatgggta   3000
attgtccttg acagtaggaa gaattaagct gtagcatgca cttcctggag aggtcgtgga   3060
atctcaggaa ttaggtttta aagggaatat ttgtaggcat cttttggggc tggtgcaatt   3120
gtaggttgga ggtgctgggg ataaggctaa tggaaatccc taccagccac tctaaggcct   3180
tctgcaagga gtcagaacca cttttcggaa gtaaaactct gtactggcag aggtcctgtg   3240
cttgacctta aggctcagag ccatgcattt ccgttttcat cttttcactt aaaatagcac   3300
ttgtggtagt aataacatgc tcttgcggag tggcacaggt ctgcatggtt atgaactttc   3360
tgtcaccacc cagcaaatgg cattttccac tcttctgttt cagattttcg ggagtacttc   3420
cttactccca aattcctgat tgaatacgac tgaaaacttc aacacgtttt tagtgcacga   3480
agtgtacttt atacaaatgt gtgggactat tgcacacaac ttactgattt tcttcactgt   3540
gtgcacatgt gctctgtgat gatacagagt ttggggtgac tgaactgtta cccagtcttt   3600
accgaattag ggcagcgatc ttaaaccttc atctgaactt ttgctagaga tgatcttcta   3660
ttttgtttag acagggttct ctgcttgctt gcatttgttc taaaacgaca gtctggatga   3720
gaagaaacca accagggctg gcactgccct acctttatt ccctggatac tttacttggc    3780
acatcacttg gcacacatgc aatacccttt tttcaccccg gtacccaaag aaaagacgtg   3840
ctcctgcaca gactcagcca aattcctgcc tgccagtgga gggcgttaca gaggcttggg   3900
gcagagggag gaaactcact cccaaagcat atactaaaaa taggccaatg cattgcaaac   3960
agctttgctg tgagagcttc cttctggcat gtagccatgc agctgcctta tagttttgag   4020
cctagatacc tccaaaacaa acaaaaagt cgctaaagtt aaatgcagcc agcagtgctt    4080
atagtcttga taatccctac agtgtatcaa ttttagtttc ttccagagtg caggtagttt   4140
actcaattta acttcaaatg tctgagttac accattgaca ccattgtcaa gactagtgct   4200
ggcaatccct gaagtctgcc aagttcaaag cagggaggag gcctttaaag ttgaaatact   4260
cgggtgacgt gtccaaaaag ttttcctgtg gctttcctgt ggagtaggaa ctgcagtagc   4320
taggttgcaa aaagttttta aactctccaa attgctgcta actaaacatc cttaaatcct   4380
gacatgagag tatgaaatga gaaagtcagt tccttgattt agactagctt gaaaagaata   4440 aacttttgc acaggactcc ctggacagtt gggctggata atagaagtga ttcattcagg    4500
tcttgatgcc tacaagtttc ttgggttttg ccatattttc cagtgatttg tgacatcatt   4560
tttgccctaa aataaatcgc atcatgtcct gccgtatgtt ttgactatga aaatggaggt   4620
ttcggtttga ataccaaact tcgttgttac ttctttcaga ggctgttgat aaaggaaaac   4680
gtgaagcttt tatgtaaatg atcatgattt ctcatttgca tcaagaatat tttccaaaat   4740
agtagttaaa tccctccaat gattttcagc tatgtcacat aaatcaccga aaacacggta   4800
attttgcacg ggtgtttttt ctcccttttt ttattgtcta atactcagct tatatttgag   4860
tcttctgtat ccaattacct gatttgtgtg gcaattaaac agaagatcag cgtcattgta   4920
cttcacattc tttttaaact catcagtagt atgaccacac tagttggtct tgtaagtttg   4980
taatttaaga tgtgcctgga aggggttcaa agagacagga gcagtagtgt gtctcacttc   5040
cctttggaaa gcctttctga tactgtcaag caatatttac atcaaaaggg aactgaattc   5100
tggtaaactt ttccagactc caagtaaacc gaacaacctg agatttagat aaaccttggt   5160
```

```
ggatttaaaa acttgatggt atcactgtct aagacttgtg ttagcccatc agatattgca    5220
gacgtatatt ttgaggaaag gctttcagtt aattgataaa attaagagca gagttttggc    5280
aaaaaaaacc gccatctctg ctcagtactt catggcatct tgaatttctg cagttagagg    5340
tacaggtgct ctgttctgca attaacccgt gctgttaatt aaaatgtact gtttgctaaa    5400
tatgattagt gtctggagcc aggtagcttg aaaaagcttc aagattattt cttttttacca   5460 ggaccatcaa gttttagcc ctcccttag aggaaggttc agaggaggtc ctatttaatc      5520
tgtcccagaa gaaaggctat ttctcccctt agaatggggc ttggcagtcc ttttcagagc    5580
acttttcatc cttgtctcat agggattttt aaggacagat ttctgaaagg attttccacc    5640
gggtaaagcg ggatcctgaa tgggtgacag ataatacgta ggaattctgg cttcctactg    5700
ccaggttgtt tatcttgaga tcttaaaaat ggacttattt ccctttttaa gtgtaaactg    5760
agttcttgag gcaccttttc cactgaagta tctgactttg cccttactgc ccatctcagt    5820
cttgcacatt taacccaaat tcagatccag ggtgtggtgt tactcctaga acagctctta    5880
ctgtttgagg atctgaatga ctattttgcc agcttgtgcc atacaactcg agaggacctg    5940
caaaggggag gggagtcctg atgggcagtt ccctcccagc ctggcatgcg cttcgtgtct    6000
ccgcttccct tataatctgc ccagaaaaga tttctgaaat acttgagcag ctgccacaat    6060
ctgcatggga ggcagcagcc ttggcatgtg agctctgcca cctgatgccc ggtctgtact    6120
gaggcagtgc cagctggatc tgcaagcctc agcgaataca gccttcgtca gcgagttctc    6180
tgatcagatt gctgccttgg agcctttgc tggtcttcct cagctcttct cctgttactc     6240
agatagcctt accacctcct ctcatcatct tttgagtttc tatcctcacg ttacagccag    6300
gtaagcccat ttaccatgc tgatatcaac aggttccaga tttttttaaaa aacaatcctg    6360 tctggctcac agctagggag cctctagtga cacagctaag tccctgcag ccatttagaa     6420 atgtttctgg agggatgcag gtacgtcttg cactcaggtg cctaatgaaa gcagattgac    6480
ctgttcattc cttcgaaagc aactaagcaa agtggggaat cccatgtctc tgccccactt    6540
ctgtgttcct gacggcaaga cctcctgcca gcaccaaccg cctgtgtttg gagtcagcca    6600
gccttccgtt ctgactgaag ttgaaggtac agtacaaact gctggctaaa gaagctgct     6660 tgacttgctt ttttaggagg cttgtcttgt ggggaaaaaa aaaaaagta cagataaatt     6720 ctgctgattc cttctgagtc acccagcagc gatggcaaag ctaggagaaa aaatgggatc    6780
acagagggat tgatgaatgg acagtgagtg acctgaagat ctaactcaaa ggacgttact    6840
tcaagtgcaa gtgtcaacat ataaatgctg agttgttgtc tccaagtacc ccactgttgg    6900
ggtatcctgg ttaccaagca aggttttagt aagtctgttc gaaaagttac atacagctga    6960
cattcatgca ggccatgatt tgccaggcct gagctctgag gtattcctgg acggttagag    7020
aggataaaat aatttagaag tcaggaaacc actcagagac aaaccattat ttataaaatt    7080
attttgcctt ctaaaagatg tgcgttccag agaaatcaca acgttggctc caacctttt    7140 gcatcatcta gctagaaaat gtgcagcttc cagataccgc cagatcacct cccttgaccc    7200
tgccctggaa acatcaatgg ctcccatacc agtaagaaca aaactggtca tctactaaat    7260
ccgttgctga tctcagctaa ccaacttcct gtaatatcag caaatatttc tgcttttgta    7320
aatctgttct tccttccata tgggggtgcc agcaggaatg cttgggatcc agaaatgcgc    7380
tggttggcag gaagaacaaa gaaattgttc acccagaagg gcaaaaaagg actaatgctt    7440
tcgtccgctt gggagaagtt gcacagaact tatgccaaca acttttgcac gcaatcagaa    7500
agatgccgct ggatgttact tttaatagca gacgttaata tcagttatta attagaaatg    7560
```

```
tcttcagtaa ccagactaaa agcagatcct gaaacactcc tgtggttgaa cagtctcttg    7620
acagacactg cccactgtcc agtaatgtca ggcgctctct gaacttgaca gggcagctgc    7680
tgtttttccc agccttctgg aaataggcca gctctgacat gtttctgata ttagctgggt    7740
gtatttcatt ctgctgccct aggcagtttg ataaaggctc cttcctcctg ctccagagct    7800
aacccaccca aactgtagcc gagcacctcg ctgcaacaaa actgcactcg ctagggttct    7860
gcctgtttgc ttcattaaga tctgcttaaa ttgtttcgta caaggaaca ctcaaactga     7920 tttctgagcc caaagtagca gtgctaggtg tacatcagga gttgtttggc atgaagaaac    7980
attgccatgg cactgtatga ataaagttat ttttaagaat cattatccct tccttgatac    8040
caagtcttta tgcggcagaa aatcaaactt ggtctccacc cttacagaaa gcagaggaat    8100
gctttcagct gatagttgct taagctagaa tataagaaac catgaatttc tgtgtgcact    8160
gcggcattgc ccttcattcc agacctacag aaaaaaacga cacttttgtt actatttttt    8220
tccttcccat atgagaccag gggagctacc caggcatttc cattcttata attttacctc    8280
aagatcaaat tttctccagg cagttaaagg cagctgcacc cggagacctc gctcagcctc    8340
cccttgcatc ccacggagct gcgtttagtg agaaacctcc cccgaggtga cgggctgcag    8400
gggacccctt cccacacgcg tccccgtccc ttttctcagt gcaaacgcag ccaccgcccc    8460
ttgaaccctc ctccgggctc tctcggttcg gcggaggcag gaggggggccg tgcccgccgc    8520 ccgggagctc ctcacagggc ccgggccccg gggcggagcg gccgcggcca tgttgagggc    8580
ggggagcgcg gaaggcggcg ccggggccgc tgcgggcgc ggcgcctccc cgctcccgc     8640 cgctcctcgc cgcccgcagc cgcaacaccg gccccggccc cggcggggccg cgccatggcg    8700 accccccagcc cctgcatcgt ggtgagtgcg ggccggcgc tgcctcctcg gcctcccgct    8760
gggcccggcg tgcggtgaac ggggaggggg gaggcggctg cggggagccg gcggggccg     8820 cccgtccccg tggggcgccc cgcgtggcgt ggagtcacct tgaggggctc gggctcccgc    8880
tgccctgcac ggccccgccc ggcccccagc gcccctcctc ggctgccggc tcggtctcgc    8940
ctcctgcccg tgtcctgcc atggggccgg cggggtgttg gcaatttcgg ggcgctgctt     9000
gggcggctcg cggttgggag agccgcgggt gctgcctcag aaggcgccca gaataacttt    9060
ccaccagaaa taacttccac caggcaccga cccggcgtgg cacaacttcc tattcctgtt    9120
gctcctcaca gcgcgctcgg gaggtcgtgc tccgtgtacc aaaacctgcg agctcagcac    9180
ccgaactggg atgccttttg gaggaagacc ccgctgaggg tgtattttt catcatcagtg    9240 tgctctgcta agaatccttt ttttttaat tattattttt tttaaaccca gccccgggtg     9300
ccgtgagcgg tagcgtgaca cgcatgtggc gcctcgcggc ccacggccat gcctgccgtc    9360
aggctgtgcc cgcgcgcctg cctgtacttt ctcgctaaaa atccatctgt aaacccacc     9420 gaacagcccg ctcagtacca aacgtagcct gcaaggctta gtggatgtgc tagatgtagt    9480 tatgggctg aaccgtagga aatttccgta gctgctgaga ggacccagc tcctgacacg      9540 cagcaggtca cgggctcggt gcctggcctg ctgcgagcag gggttgtgca ggggctgctg    9600
tggctgggag ggcaggcctg gctcccgcc aaatcctca ttaccgcttg cgcaaccaaa      9660
aaacatgtaa acagctggct gatcacaggc aaggtaagtg cttccttggg cactgaaatg    9720
gaagcgtgat ctgcaccggc agcggagctg aggtggatgc ttaccatgcc tgccccgctg    9780
cattgccagc agcaggcttc agtgttcccc acaaacttct ttttacactg agcagccttc    9840
agctgcgtaa ccaacaagtg aagcgattca aaatatattg tcattttcaa gtggcagcgg    9900
ggctaaggtt caggggaagt tttttcttgg tgcttttgga acaatatgcc ctgaaccaca    9960
```

```
gcagtggttg tataattacg tacataggca aacccctttgt cctaattaat acactcctgc    10020
taatgttgca agctgtttca tgtggaaaat ctgcccgtgc ggaacaggtt gctgaaacag    10080
ggctttaatt tctgattcta aagatcttga acctccactg tttccagatg gtggtcagag    10140
aaggcttgtt tcataggcac ataacttgtc ccgttaatat agctgtcttg tcttgtattg    10200
acagctggct tgtatgtttt gttgtgattc ggtgttgtgg agatttggaa gatgtccctg    10260
ttacaaggtc tgcttactta gttgcaaagg caggttttgc attacactgc tgaaatcaga    10320
gatgttgaaa agctgaaagc tgcttgatcc ttgtttattt atttattttt aaatgaaata    10380
agattatttg aggtgtagta atttcatttt ccccgctctc caatgggggg aaatgttgtt    10440
agggcttgaa atcatttccc ctccacatcg tgctgagcga cagctcatgt agcatttcag    10500
acaactcttg tgaactgtgg gttgtgcaag cttccacttt gtgctctgtt cagaaggaaa    10560
ataaggtgat cccaactagt gtaatggatt tggtagttta ttgagtaaag caaaggattg    10620
gcagtttctc actacaggct ttctataaga cttttgtagaa atctcacctt atttcctttt    10680
cagattgacg atgatgaaca aggttacgac ctggacttgt tctgcatacc taaacattat    10740
gcagatgatt tggaaaaagt ctatattcct catgggctca tcatggacag gtttgtttga    10800
cttcagacag tacactgctc cagctgattc catgacactg gaaaaaacaa tcttccagtg    10860
atagttttgc tgcctagtga ctgtctaaac agattacatt taattagaga ctaagaaata    10920
cacatgttaa ttaactctct cttgtttggc ttcaaagagt ttgtacattt gcagttacgc    10980
tattgtttgg aaatttgtca attctcaaag aaatttgtgg tacgtagcag tctgtgactt    11040
tctttacagt gtttctttga tgttttactt aaagtaatta gaacacatta cttgttgtgc    11100
tagttcaatc taaaaacagt tatagtctct caaacatctt taggatatta ataagagtag    11160
attattaatc acattatgat aagactttt catgttcatg tggtagataa ctaacaccca    11220
attttcccct actgtctgcg aaagacatta gcctttgcaa ataccaatct gtcacttgtg    11280
gttgctgaaa tgtatgattt tctctggaag ttttatctcg tgatgagaaa tgggtacatg    11340
aacctataag gtgttttttgt tttactttgt gtaagtaaag tggaggagtt gctggagaca    11400
cagaaccact gaagagcggt tctgagtaga tcttgtgaat aggaatgctt ctagattttg    11460
catggtgctg tttgatcaga ttattacagt atttataata aatgttttt taactttaca    11520
ctgaaagacc ctatatagga aagcattgga caaagtacag gtcattaagt agctgatgta    11580
aagtttgtaa tggcaggcat tctctgagaa acctgctgtc agctgctata ctgtaaatac    11640
ataccatgct ttctgaatta aattgcaaga taaatttaga acaatgatc actgaaaaac    11700
tgttcagtgt tctcttgctc tgctttattg gcattatatt ttgcagtcag gacaaattta    11760
ttcagcaaaa cataacgcta tagttgataa tttgagagtt ttcttgctcc tcagttagtg    11820
agagctgttg tcttttttggt tgtgctgatt tattttgctc tctgcatgga agctgaacct    11880
atctttggaa gaagaaaaca cccttatgtc tcttatctga cagtaaaaca attcagggtg    11940
ttcagatttg ctttggctga gtatgatgta tgaaaacaaa gaagtttggc agtgttactg    12000
ttagattaac cttggaacgc aaaactttgt tgaccaatag tgggttaaag tgactgaagc    12060
attaggcaaa tatttctgag caaaatatgc ttccgagttt gcatgtgttt gctgttgttg    12120
tttgcaatac aaaatactgc tgccatagta agcaaactaa atgtgttaca acagctaact    12180
ctctttttttt tttttttgta taggacagag agactggcac gagaaattat gaagggcatg    12240
ggaggacatc acattgtagc tctctgtgta ctcaagggtg gctataaatt ttttgctgat    12300
ttattagact acatcaaagc actgaacaga aacagtgaca aatcaatccc catgactgta    12360
```

```
gacttcatta ggttgaagag ttactgtgta agtatctctg caataccatg caatttttct    12420
gtaaatttga ctaacttcaa attaacaaca gggatgattg agaattgcca acaaatgttg    12480
caaaagcttt gcctaagtac tgcctaaatt gtgctaattt tatacaaata gttaagacaa    12540
ttaagggaa aaaagcagtc acaagctaac ttgttctttg tctatcttat atgatctggt     12600
ttctttcaga ctttatctcc tcggcccagt aaaatccaga gcaaagagac cctttccatg    12660
tcctttactt cttaaacaat ttcctctctg cccctgtcc cacctctaaa actgtggttc     12720
tagaataata cagaggatag tcctacaaat cttattacaa aaacttaact ctaggaattt    12780
tcatgtggct tagacatcac tcaccagata ggaaaacttg aaaactgtga gcatggttat    12840
atttgggttc cctacctcat cttttgtttg gctcaactga acaatgaatg gaatgaattg    12900
catttggcca tgaggaaata ctagattcat aaaaacagat ttatggttag cggccactga    12960
atatggtgct accttttaaa gcctaggtct aggttgcctt ggctttatgc ttttggaaaa    13020
gaatttattt tcattttgca cacaagtatt taactttaca gggaaatgga gcatgaggta    13080
gtatgtaaga ttttttataag ggaagcatta gattacattg tgcaggtcaa aggaggaagc    13140
agatgtatgt tagtactgta tgcttcctga ctcagcaaca gcctagtcta tgttttcaa     13200
gacagtattt gtgggtaatt tagattttttt ccataagatc acctgtagtg tggaaataat    13260
taagttttttt gatttcaatt tacggtgtca aaataaattg cttcttaagg tcatgctgtt    13320
agttctgtgt ctcgatgact gtgttttcca gtcagtagta taagctactt gtcatggttg    13380
tggagtagtg cctgctgcag tagaaaaaaa tagattacta agttggaaac tcaactgcat    13440
tgttcattta attaaaccag atataggggt acttgcagat ttaggttgga ctgtagaaga    13500
gcttcaaaaa tgcgctgctg ctgttgagcg atctgtaaaa atttcacctc gttgagtggc    13560
aaagctcaga ccagtcagag tttggccagg cctgtttgca gaaaagctgt gccagctccc    13620
aaggtgtgtg tgcagtgatg tcctgggggct acctggaaac caccgtcatg tctgcagagc    13680
gtgctgcagt gactcagctg cactctttaa agagaaggca aggccaggca gaaagggaca    13740
tgccagcctt tcgttacatc ttgcaagggg agagctgctt gacacacttt gtttctgctc    13800
cccacaaaag attcaggctc cctctaccag tccattcaac cacaaagcca ctacgtgccc    13860
acatacgctg tctgtaaaag ccacaacaga aaggtgaatg tctctattag aggataatat    13920
ttgaaagaat aggaaataac tcccacctttt tttggcgagg aaatttgtat ttctgcttt    13980
cttcaaggaa cacatccaat aactttggtt tatttaaaat ataaggacta caccccttctg   14040
ctctctccac cttccgagta acttggaaca agctatggga taagtgttgt gaaacacctg    14100
gaaaaaatac tacattgcaa agcaaggctt attgtacagc atgttttat tgttcatctt    14160
tatgcattag gcatgtattg gttctgctgc ttttattttt tacaccgccc ccccaaacta    14220
tagtgctttt atattaatag gaaactgaac agcaaaataa ttacggaagt tttaattctc    14280
ttttttgtagt aagaaggagt aaacaaagag aaaagcagag aaatttacac agaaaggagt    14340
gtaagcagaa tgttttccat gaggtgttgg cttcagggtt ttggttttgt cagccaattc    14400
tgtaaaggaa tgttttcttg ttctatatga ccgaggagct ccagttactt gatggcccca    14460
ctagcagatt attacgagca tttcatttct gtcaactctc taaggtagtt attaatatcc    14520
agacttacgt tctttagatt gcataacttg atagactggg taagactgtc ctaacacaaa    14580
catgcgtgta attgattcac ttagttttcc attattaatg gtgctggaat gttaaatctg    14640
ctctgtagtt tcattcgtg ctttactaaa cggaggagtc agcattctta atgatgggaa     14700
aaccatcaca aaccgtaatg gacagttgaa agtagagcta gctctcttgt gattgttgtt    14760
```

```
ggatgcaatt actagatcac gctgcctgcc tttacagact gggtgaaaga tgttaaaaat   14820
accgtcgttg cataaacaaa gcagctgaac tcgtataatg gttctaaaat tgatgcgatt   14880
gatgttctat tcctatttga aattgatcat ttaatatttt caagcttatg ggttatttgt   14940
ttcataatgc aaagttcata ctatgattgc acccaaaaat aattctctaa gaatactgag   15000
atgatgaagc tgtgattaaa tgttgcttat aattcctgct ttcggagtcc ttacaaatga   15060
gttttaatga tctggcaagc tgttaagaaa ttgaaagata tgtttgtga  acagaaccag   15120 atctctgtat tcttgacaaa tagtttattt ttcttgtgct agaagaatgg cttttcacca   15180
gtttcctgca tgtaaagtta gagttaagca aaagttgctt atgtagtcac aaagggcagc   15240
caaaacacaa tggacgtgtt gcattgtcac tcagggaaat agggcttttc ggaggagtac   15300
tgcagcttta aggcaaaatc tagttaggct ggttgagaca gtattctgaa agatctcatg   15360
ttaactgagc cttatagcaa ataccatgag gaacttaaaa tgccttgtca ggggttacga   15420
tcttgcagca tgttattatt ttccagcaat gacaatgagg cagtgaaaac agatctaaac   15480
agtaaatctc taatgtgtta aatcacaaag cattaaagtc ttaccagtac tgaaatcaga   15540
aataatgctc ctgaagataa ttaaagtgtt gcttaattat aaacaaagt  tctttccaat   15600 ggaaatctgg ttaaaaccag tgttggaaat ttgttaacca ttttgatcc  tttaattgct   15660 cagaaactca gtacctgcat aggcgtgtag gtttatatgc cagcgaaggt ttatgttttg   15720
tgttaaaaaa tgtagcaatt tgcagggtgc ttggtgggaa gaagaagggc agattttgtt   15780
ggttagattt tttttctctg ctgatcagtg tacttgagta tgcataaccc acagggttct   15840
gtagtgatct gtagttctgt gttgttattg tttgattata gtgtgttgct ttgtagccag   15900
agagatcacc aggaaactga tctgcatgca tgtactgaga ggactggtct atcatctgtg   15960
catggtgttt taatggaaca aatatctgta acatctttct ccatcttcct tctgtaagaa   16020
atggtgcttt ttcatccctt ccatggaaaa aggacgaaat tcttattagt gtaggaatag   16080
ataagagaga atcctgcaac ataaacaggg aaaagcttaa agctgtcatt taagataatt   16140
ttaagatatg atgaacgcag gaaatgcccc tcagcattac aaaacacggtg cttaactgaa   16200 tcccatttc gtgattaatc taaccagtat ctctggcatt cagtagcagt ctgctgttta   16260
ctgggtcaag cagcagacat tttggacatc ctatttttgg acttttttcaa cacagtggta   16320 ttggttctgt tcactatagt tttctttaaa acatggggta aaactgtaaa ggcgcttttt   16380
ctaatgtgtt gtgcttgcct ttttttttaat gttttgtcat gggaatctaa aatagaaagt   16440
atctgttagt ctcgttatct gcttttacat acctagagct gtcagcactt ctttatccta   16500
gagcattgac gtcactgtcc aagggatttt aatacatttt ctctttactg taatcccagt   16560
gtcacttatg gtgtgctcag tgtgtgtttc tctctaaacc atttacccct ttttgcatg    16620 tgataacact tctactttt  gtctgcaact ggtacagtat gaatatgtgt gtcagtgaaa   16680
acaggaagct gtatgtggcc gtctgttccc ctgtggtctc ctctctattg tatctgccat   16740
tttggggcgt ggggaaggaa ctgctctttt gctgcttgtc tgcatggtca tgcagtaagg   16800
ttgggcttca gactgaagcg gcaaaataat aaaggttttc taagggaag  atatgaagtg   16860 aagagctgtg agaatgaagt ttgaaaagtg gtatgaccct tcaaataaat gattaaattg   16920
taggataatg acatcatctg taagtagcac agtaatgagt atagcacaat taataagaac   16980
taggagacaa tgtcaaggtt taaagtcagc tgaatgactt taaataaact gcagagatct   17040
ggaggtaccc caggagttgt ttttaacttt cttatataac aaacagttca ctgatgctta   17100
catcaaagcc tagtttttact aaagcaaaat gctgtacttc agtgatagga ttgtgtagct   17160
```

```
gtgtcgctgt ttaattacca caatgagtaa tttatcacta tttgtaaaat aggcaaaccc    17220
aagcttttct ggctattctt gtagcttata tttcttgttc ttaatctgtg ccttgtttgc    17280
tggctatttc attgttgtta tgattgctta tttttattca gagtaaggct ttctaaggca    17340
tcaaagttta aaatgtaaat taccagctat atagcagcgt acagcttgga aactttttt     17400 ttttcctgtt ttccatacct ttaatgaata tgtaggaaat aatattttt taatatacat     17460 gtgtgtatat ataatggtga cagatgagaa gtggtgcctg tatttatgta aatattttt     17520 caaacaatct tttatctgaa ataccatctt tcagtttgat tacttgtaat tcttagtta     17580 atagatgttg ctggtgcaat gcttctgaaa gctttggtat ttgtgggtta tgtactttgc    17640
agttttgata tttattagaa gaaaaattac tttaattctg gtaatactaa tgcttaccct    17700 gctcttttctt gctagaatga tcagtcaact ggagatataa aagtcattgg tggggatgac   17760 cttcaacct tgactggaaa ggtatggcat gtcatatgtt taaagcaacc ccctccccg     17820 cagaaaaaa atcctaaaa aatcctaaaa aaaacaaaa caaaaccaaa aaaaacaaaa       17880 caaaacaaa ccaaaaaaaa aaaaaacacc aaagaaccaa ataattagag ttttagaaag    17940 gaaaaaaaa aaaaagaaa gaaaactgta gtgtttcatt taaaatttag gttagaggtt     18000
ggacttgatg atcttgaggt ctcttccaac ctagaaattc tgtgattctg tgattctgta    18060
aaatattcac cattgtagag tggtggggtg cataagcccc accagagcca tcagtttagt    18120
ttgaacttca taacatatgt atgtatattc actgtcttca gtatcaggaa gtgttagagt    18180 tgttttctg cattgcctaa gaatagtctt gtcttggttg ttgttaacaa agtaccttta    18240
aaagagagta gcgttactta ttactgtgtt ggtgtttcat tgcaatagtg aacagagttg    18300
gtactgtcta gacatataac ttgcaggtta gggaataagg gtcctgttac aggcaatgaa    18360
gagacagaaa tgcagagaat gtaaattggg aatctgcttt tcttcagtgg ctgtgtagag    18420
atcattgagc tagatatctg tgggtaaaac atggatgcct cctgttctgt cagaacacat    18480
ggctttcccc ttctgattac acataaacag tctctgtccc atttcagtgt aagtgatgta    18540
ggtgtgacaa gacagtacat aactttatag tatgacattc tctgcattat aagaatttaa    18600
aggccacttt gtactcagca tgagatgttg aggcaagtct cattgtcaac taattgtcat    18660
tagagcatca gaaatgttaa ctaaatagaa ttcactgtta tgtgtcctaa catacataaa    18720
ccatggtaca aatatttaac tgcattgaaa aataaaattat taagttatag gagacaatat   18780
atgtaagaaa tgctgtattc tttaaatgct aatggattct tctttttttt tttttctttc    18840
caccagaatg ttttaattgt agaagtaagt attatgtttc actttgaagt tctaacgtgt    18900
gactggcaaa agaccttaaa cagaagttgg ttttaagtca gaaatcctac agtttctggt    18960
ttcaaggttt ttagtttctg actctaggcc tgaattatgc aagtggtctc tgaatttgaa    19020
attacctgtg ttttgaattc tcacatagca ttcaactata ccaaatttaa caaggaaaat    19080
atctgtgtaa aattgcttgc tgtttgcatt tgatttcagt tttctgtgat tctgtcaatt    19140
cttaaatgtc ttttttttt ttttaataat tcttattaag aagtagcctg agcaaagtgg    19200
tactaagtgt gttattgttc tgagtttata acagcaaact aggaaattaa actgaggggg    19260
tagaaagaag ttcctagtag gaatatccta aaatacatgg gaaaacagag ctaaggccaa    19320
catctctgtg tacagtttct ttacaggcat ggagaatgtt gattcctaat ttgcattttg    19380
ataatgctta attcccattt ctctatcttg tcgtggttct tgatactag gtacaataca     19440 cttcagtctg atttcctagt agctactgtt gcttaaatct tgcttccata cctctttgat    19500
gaacgatgtt gcttacattc agtaagtatg acttttacaa aggatgatct agaataagat    19560
```

```
cgctaacttg aggttggcaa agcagaagta ctaaacagga aaaatgaatg tatagaagta    19620
ataatgtctt cagactccaa atagtggaaa tggctttgtc cataagctat ggcaactgat    19680
tcagacacca aatgaaagga tgtttccttc tgtcattaaa tgtgtttttt ttatgtacgt    19740
cttttttaa tttgagaagg ttatattatt ccataggaaa cacttttgac ctaaactgtt    19800
ttagttcagt tctaaaactc ctaccaaact agtatgtata cagcagtcat ctgtgtgacc    19860
ggtggcgtcc tttgaagtgt atttgcttca gataggcaga tgcatttaat tacgtatctg    19920
ctccatttca gatgaatgta tgtcttcaaa gtcccaggca gctaagtagg ttagtttctc    19980
atctgttcag tgaatcatct ctccagtgcc ttatatataa ttatacattg tcaaatatga    20040
acccctttgac cagtcaccgt tttaactgtc aaacaatggg ggaaaacaaa caaacaaaac    20100
caaaaaacat tattataggc accagagcac ttaggttttc catacagaat cccctttgatg   20160
tataaaaaca aacaaacgaa aaagaagaaa agaatcccat cccctttctgt gcagggggatg  20220
ggattaagat ggtgtgtcaa acatcatttt agtgtatata aatagaaact ttagaactgc    20280
acccagatat tgccagtgca gcttctttgt ctttggattt ttttgggtct gtaatgtaag    20340
ttgcacttct ttttccttta attgcattga tgggttgttc tgaatgtttt cccgtcttat    20400
tttctttctg ttgtatacat ctctctctga gttcaactgc aagactaatg ttccatttat    20460
aatactggaa ttaaacaatg tttgtcaaat agctacaagg aacacaagcc ataaactctt    20520
cagagggagc ctagaaggtc atagttcagt aactgctttc aaagtagtag ttatctacag    20580
ttttgactgt tgtgatcact ttactgagca taattgctta agcacaatat agcgttatgt    20640
atcacctgta tttgattatg aacattattt tgtcatattt ttgtgctatt acggatgagc    20700
aatttctgca gtaaaaactt gaaaatgcta ctctgaaaat tttaatattc tcacttacat    20760
gacactttta ttttcaggat ataattgata ctggtaaaac aatgaaaaca ttgctgtctc    20820
tactcaagca gtacaatcca aagatggtga aagtagccag gtaaacttct aaatgtgatt    20880
atttgtgctg tatttcaact tcagaatgac acacagtgga ataaaaatat aatatagaat    20940
atattcccat agaagagaaa caggaaggaa catttctgca ggaatcatac atgatggagt    21000
tagagttcag tatttgtttta aactcaactt ctgcttgttg tgggagcata tgttcattaa    21060
ggctaacaga aatgctcttc tttccagtcc tattgcttga aaaatatcag tgccttatat    21120
tctagtaata tttgtggggt tttaccactg atctttaact taggtttaaa agcatatgga    21180
agaatttaaa tattttgggc ataaaaaaac acaacaacct ctcaaggtgg caggggtatt    21240
ttcaacacaa atttagttca taaatataaa ctttataaat ataagttta actagagatt    21300
gggattaaaa aaaaaagtca gtggttgacg tctatggaca tacagtatct gaacatgttt    21360
cagtttgcaa cttcattttt tttcagtggt gtatctgcaa tggagacctt tggtctgcca    21420
gctttacttg tagaattaaa ttagtttgca ctaaacatta ccgtttatat agagtatata    21480
gtgtagctga gcctcagagg tcattctgtg agtcacccag ccatatgctc ttttaggctt    21540
ttctacttag ttgcatcttt aatcagttag ttatgaaacg ttttctaatt aaataactta    21600
cagttagtaa gaaatgttga gggtaatatt aaccatatc aacattcctc ctacttcttt    21660
ttaaattgca tcttttatgc tcctatgctg tgattgtgta ttttacaata aaagcataat    21720
gattgctggg gattagagat aaaccagaac tgtgtgtaaa atctaatcag ttgtgttgcc    21780
ataacaatgt caaggcagtt gttagatgta ctagagcagc tcttcttgat gataatgtgg    21840
ggatgacctg ctgaaggtga ggttttgtt tttttttct ccgtggcctg cttaaatgta    21900
ccagattttta aatatttgtc actgaatagt accttaacgc tacagtgtac atcacaagta  21960
```

```
gaatgcagca tgaacaaagc ctagcttccg attgtttaaa cctgttgcag tttgggtctg   22020
ccgaagacct gagcaagtaa gcgtgatcgt gctggatagc tttaagtgtc atgctcttag   22080
ttcacttgcc tttcttttct taattttgtt ttctttctct ctgacaatta agcagttgta   22140
gcagggagat gtgaattaat gctaatgtga ttttgggttg gtttgatcaa gttttatgcc   22200
actactcaaa ttaagactct caactagaag tttcagaaac tgaatgtcta aagacagaca   22260
aatgtcagga tgatggggtc atcttctgaa agtgtgcaac tgaataatga gtgagtcaaa   22320
ttaaactaga aaggtatttc attctgctac agtaccccca actctgcatg tctatgcttt   22380
ttacacctct gactattaat tctgtgaaag tggagctggt ttatatcagc ttatgatcat   22440
caaaaccaat tacattttct gtatgggggt aattagtact accagtggaa aaacagctga   22500
ggacatgttg cacaagtgca attgaggtta catttaacca gctgaacttt tgcttcataa   22560
cactaacgct tttgaaaaga cctcagctgg tctggctaga tcccaagttg tcacctcttt   22620
acctgcgagc taaactgatt gcacctgagg ttttctaaaaa cacataaaac ctaattaagt   22680
cacttctggc aatgaaaatc cttccagtaa agtatctcac agcctctttg ctgcaaacat   22740
tttgtttatc ccttaggctg taaaccattc atgattctag gaagtttga gtttgtctat   22800 atgatcagct gcacctgcaa atgaataata tgtttaaaat gtatatagtt atgctgtcaa   22860
ttatacacat gtagtctcac tgaagtggaa ttcagctaat cttcgtgttt catataagtg   22920
aacctggtgt ttttccacgt ttcagtttta cattgttttt atttgacagt tgttggtaa    22980 aaagaactcc tcgaagcgtg ggatatcggc cagactgtaa gtgacttttt gacacccatt   23040
atcagttttt aaaaatatgt tgtatatatg ttgatgtatt gtgtactctt tggtcaaagt   23100
ccaagggtgt tccaagtaag ttttcatgaa tggttttttga tttatttgc tcttatttgg   23160 gaagtttaaa tatttggaat gtattttgac agagttaata cagatttggt ctagtccttt   23220
ttttcttaac tttttgtggc attttattat acaaaaagga aactttgata ttttagtcca   23280
agttaatccc tcttcatatg gaaattctcc tagcttgcac gttaatcaaa tggtttggtc   23340
agcagaagtg tcatctttga cacttttggg agtgttccag gtgcctaaac atagccaccc   23400
agtgccactc ggatgtcccc agaaatgtaa tgggaccaca cagggtaaca gatctgatca   23460
aagtttacag tggtaagatg ttcaaagtag cacaaacccc atcttgttta agcatctgga   23520
ttactcctgt catgtcttct tgtctgtccc aagaccataa aggaaggaag agcatccaaa   23580
gcacacgggg gtgtcagtga tagcccctct tggcttggaa agggctacgt gtgctatccc   23640
tgtgccagag gttatttcct gttcatgtgg actgtgcgct ttcacaatgg aagtttaaca   23700
gaattgcatc ttcttttcccc tccttttccaa gtttgcacag tattcttaaa ttgaaatttc   23760
tcagtgcctt gaaagcttaa ttcaggtgtt tccctcactc gaggatgcct ctctttcctg   23820
agatcttatt atgggtttag ctgggttaac agtctgcctt tctgagcatc ttgcagcaga   23880
tgacttgttt tgccatctgt ccagagacga cctgttcagt gcagaacccg tgagctctga   23940
aggcaagaga caacgcagca gcagagcttg ggcctgcctt ctgtccttgt atcatgaggc   24000
caagtagact ctaaacattg ccttatttt tccagaagcg tacacagtct ttcactggaa   24060
ttgtgtgatt tatctccgtt ttttcatta ctgagcctcg ctgtaaccag ggagagagaa    24120
acagcacagc tcgggagtct ttcatgttta gcataagggg agaaagcctt ctggaaacgt   24180
ccttaggttg tcttacagtg tgtgtggatg gcttggactg atacttcttg actatccaag   24240
gactgttctg ctagagccat gtccacttgg actatctgtg gaacagctga tgtgtttttt   24300
ttaggcagct tctatgggaa aaaaaaaaa cgaaacaaaa cacaacaaaa aacccgccgg    24360
```

```
tttctgaaaa gtgcaagtga caccgtaaat aagagagcgc cttttaccct gtggtcttca    24420
ctattctcta taccaagggc ttggcactta cagcgtgttg ctctgcagag ctgtcccgca    24480
gtcagagtat gtcctggtac accaggttgt tgtccacgag cagccagagg ggagtgaatt    24540
ttgtttggca ctgcctcaaa gacaaaggac tggttcccct gcggtaactc tggttcctcc    24600
tggtgttgac gtgttccatg cttactctcc cagctcttca caaagagccc agttgggctt    24660
gcacacctgt agttttgagg gagctgagag ctgaacctat ctgctcgtta tcccagaggt    24720
gaccttactt atagctgtgc ccaaggcgag ggcacactca cacaggtgcc acctttgaa    24780 taatactgtg agggtgacaa ctaaaacaaa ataaaatgct actgcttggg aaccagtaag    24840
taaatctatt tcattttgtt ttagttgaat taaatcaaca aatagagtta gaccattaac    24900
tagcttgaat attaatctcg ggatacttga atggaagaaa tgaaatgtta tgcttatatg    24960
tctataaaat tctagattct ctctgtaaaa aggtctagtg aactctagga agttcttttc    25020
taacatactg atgacttatg ttcttttttca gttgttggat ttgaagtgcc agacaaattt    25080
gttgtgggat acgccctaga ttacaatgaa tacttcagag atttgaatgt aagtaacttt    25140
tcccgtatgt ttttgtccat ttaaaactag ggaggaggaa ggaagggaag tctcctcgca    25200
tcactctttc tcttctgtgt aaatcacagc tcatgtgcaa gcctgttcca ttagtgatgc    25260
aacgacgaga gcaaaggcta gaccagcaca acagtgtttt ggagctcata tgaaactaac    25320
ttttgttttg cttcatgcag aatggaggta ttctgcatga agctgtcagc tttgaaatac    25380
tgtggcagtc tgtatgaagt ttcttatctt accagacata tctgcaagaa acaagtgcat    25440
ttccttagtt acatcaaaat tagagaggag agaccttgga tgttgagatg tttgcatttt    25500
atgctaggtc attattaatt tttcatctgg gtctcactaa ccttataaca gacatagggt    25560
aggagagaga gagaaagtcc agtgttgaga tctgtagaca aaaaaaaaaa gaagctaaag    25620
tttttctgca taaacaatat cacaaggctc ttcggtactg aaatgtgtat agcatgcttt    25680
tatttttttc agaagtgcat tattgaatac atctgtaaac atcatcctac attactttct    25740
aacaggagct ttttattttg ttttgttaca gcatatctgt gtgatcagtg agacggggaa    25800
gcagaaatac aaagcatgaa agcatagttc aagtgctctg atagcagagc tttgaaatgt    25860
tttgtttact gagtcctatc tttcacaggc ttcaactctg gtacaccagc taaaattgta    25920
gaattatcca ccccccttgt catatgctta ctataactta ttgcatgtac aatatacaaa    25980
tcttgtcttg ttcatttata ttttagaaat gtaaacaatt agtgcaattc tgcactcctt    26040
attttgattt gcactatgac tctaccgact attgctgccc ctggttgggt tgtgctgttt    26100
gtgagctccg gagtctaact cttgcagtgg taaattgctt aaacctcatc aacccagaac    26160
tgaaatagtt caagtactgt aaatgtaaaa cactttatga tagggaagtc tattagtaat    26220 attttttaaaa tctgtaattt aagttttata ttttcatgaa caagtgtgat tgtgattaat    26280
ggatagttgc acctttgggt gttataaaac atgaggagca gccagttaca gtatctgtaa    26340
tcaccaagga gctgattcaa gcctcctgga gttgcttat cgctgtaaaa gtccgggtaa    26400
aaaaaatctt ttttttttta attttttta ttttttgagc taaaggaga tggaatgaca    26460 aagcagaatg tttaaaatct agtttaagtt gagctattca tttctttttgg attttttctt    26520 taaaaatacc catcagacag tgaaattgcc tttaaattt aaacaatttt aatatatttt    26580
tgaagaagta ttgtaatgtt tactttataa gatctaaaaa acaaaaagta ctttaaataa    26640
aggctgtctc tttaaaataa gccccataca tctatgccac tcattctgta tattaaagtg    26700
ctcttgaaat tttcttagta atattttca taagtgtttc tgacagtgaa ggcagactct    26760
```

```
acgtttgtta tctttgtaga gcctttagtc agtattgtgc catctacaag agatgataaa    26820
ggcctgaggg aaagctatcg aaatacttgc gtattctata accaaactgg atttcagaga    26880
aaatgcacta agtagtgtcc cgtattctgt tttggc                              26916
```

<210> SEQ ID NO 3
<211> LENGTH: 3915
<212> TYPE: DNA
<213> ORGANISM: Cairina moschata

<400> SEQUENCE: 3

```
atggcgggcg cggagccctt cggcgccgtg ctgggcgccc tgcgggactg ctacgcgcag      60
gcggccccgc tggagaccct cctccggggg ctggggagag gcggcgccga ggaagccgag     120
gtggtgcggg acgacgacgc cgcctgctac cgcaccttcg tgtcccagtg cgtggtgtgt     180
gtcccccacg gcgcccgcga catccccggg cccttcagct ggagcagtt atctagtcag      240 agcgaagtca tctcaagagt catgcagagg ctgtgtggga aaagaagaa gaacatcctc      300 acatatggat actccttgct ggatgaaaac agttctcact ccaaatcat gccgctctca      360 aacgtgtaca gctacctgcc caacaccgca acagaaacca tgcgtatcag tggcctctgg     420
gaaacgctgc tgagcaggat aggggatgac gtgatgatgt atttattgga gcactgtgca     480
atctttatgc tggttccccc tagtaactgt taccaagtct gtgggcaacc aatttatgaa     540
cttatttcgc aaaatgtaga atcagcccca gcgtttgtta acaacggct tcaaagcac       600 aaacgtagta gcttgcttaa gtatacgcag aaaaggctaa cgtttcacag acagtatctt     660
tcaaagtcac gtcagtcgaa acgcaggcaa agacttgaag ctaatgtctc cagcatgaga     720
aataaaacca gcaataatat acaaagccta gggtccgctg ctctggaaaa acagagtagc     780
tccaatgcag gtttgtcagc tacagcacca tccttaaaaa ggaagcttgc tagggaacaa     840
ctggaagtca cggctaagag agcaagatta aagagaaag agggagga acaggcttgt        900 aatactgctc ctaatgtaaa ccagagtatt cccaagaggt atggaaccag ctgtgtagca     960
tcacgttctg taagtcttat taagaaaaa tacatttctc aaagaagtaa cagtgatatg    1020
tctcgtcctt ctttagttca caattctcat catgggaaga agtctgtggc agacaaaagc    1080
tctttcctgc aaggagctga gagtaacaga catttaaagc ccagcattga aatgcaagca    1140
ggatccagca ggaagagagt agagatacac aggcctatac ctcggttgga ttggatacca    1200
atcgaaccgg cggaaagtag ttcttcagga cacaaaaagc aggaaagtcc cctagctcat    1260
ctggcagagg agttaccaaa tagggttttg ccatctacaa tatacattga caggaagttt    1320
cttctgtatt ctcgcaggta ctgggggaa cgtttcccaa aatccttcct attgaatcgc     1380
ctgaaggata gtgaggcagg tgtaaagcga ctaatagaaa cgatattctt aagccaaaat    1440
ccgtttgggc aaaagcgcaa ccaaggtctg ccacagaaaa aatggagaaa gaagaagctt    1500
cccaaacgct tctggagaat gagaagtacg tttcaaaaac tcttaaagaa tcatggaaag    1560
ttcccttacg tagctttctt gagacaaaat tgccctcttc ggatatctga aaccattttg    1620
ggaaaagcca agctgctcag tcgggcacct ttgcctgggc aagcagaggc tcacaagcaa    1680
gcagaacagc ttgggaagga gcctgctaag cgtgtggcaa gcagcagatg cgaatctggt    1740
cacaccaacg tgcccagcag cgtacgcgct cctctcgcag catctgcgtg cgtggagcca    1800
gggggggagg agcagatccc tgcagaggcg tctgattcag tcctcaggga gcttctcaag    1860
gagcactgca gccacttcca ggtgtacctc tttgtgaggg agtgcgtgga gcgggtgatc    1920
cccgccgagc tctggggttc aaaccataac aagcgccggt tcttcaagaa cgtgaaagca    1980
```

```
ttcatttcca tggggaagta cgctaagctt tccttgcagg tgttgatgtg gaagatgaga    2040
gtaaatgact gcatgtggct tcgtctggcc aaaggtaatc actttgttcc tgcctctgaa    2100
caccgttacc gtgaagaaat tttggctaaa ttcctatact ggctgatgga tacgtatgtt    2160
gttgagttgc tcagatcatt tttctatatc accgagacca tgttccagaa aaatatgctt    2220
ttctactacc gaaagtgtat ttgggccaag ttacaggaca ttggaattag aaagcatttt    2280
gccaaagtac agctacgtcc tttaactgca gaggagatgg aagcgatcca tcagaaaaaa    2340
taccttccta tggcatcaaa gctccgtttc attcccaaag tcagtggact aagacccatc    2400
gtcagaatga gcggtgttgt tgaagcacaa acgttgagca ggaaagcag agcaaagaag    2460 atgaatcact acaacatgca actgaaaaat ctatttagtg tgttaaatta tgaacgaact    2520
ataaacacca gttacatcgg ctcttcagtg tttgggagag atgatatcta caagaagtgg    2580
aagacatttg ttaaaaaggt tcttaaatca gatggtgaaa ttcctcatttt ctactatgta   2640 aaggccgatg tgtccagggc ttttgatagc attcctcacg ataaacttgt ggaagtgatt    2700
tcacaggtct aaaacctga gaaaaaaact gtctactgca tacggcgcta tgcagtggtt     2760
atgatcactg gaagtggaaa aaccaggaag ttatacagga gacatgtttc tactttcaag    2820
gattttatgc cagacatgaa gcagtttgtg tcccggcttc atgagagtac ctcattgcga    2880
gatgcaataa tagttgaaca gagcttaact ttcaatgaga caagtgccag tctatttaat    2940 tttttttcttc aaatgctaaa taataacatc ctggaaattg agcgcagcta ctacttacag   3000
tgctctggaa ttccacaggg ctcccttttg tcaaccttgc tttgcagctt gtgctatgga    3060
gacatggaaa acaaattatt cagtggggta cagaaggatg gagtcctgat ccgtctcatt    3120
gatgactttt tgcttgttac accacactta acgcatgcaa gaactttcct aaggactcta    3180
gcaatgggca ttcctgagta tggcttttg ataaaccca aaaagacggt ggtgaatttt      3240
tctgttgacg atatcccaga gtgttccgaa tttaaacagc tgccaaactg tcgtttgatc    3300
ccatggtgtg gcttattatt ggatacacag acacttgagg tttactgtga ttactccagc    3360
tattcctgta cttctatcag atcaagtctt tccttcaatt caaacagaac agctgggaaa    3420
aacatgaaac acaaattggt tgcagtcctt aaactgaaat gccatggctt gtttcttgat    3480
ttacagatca atagcgttaa aacagttttc attaatgtct acaagatatt tttacttcag    3540
gcttacaggt tccatgcctg tgttattcaa cttccattca accagaaagt taggaacaat    3600
cctgatttct tcctcagagt catcgctgag aatgcatcgt gctgctattc tatgctgaaa    3660
gctaaaaatc cagggtttac tttaggtaac agaggtgcat ctggcatgtt cccttctgag    3720
gcagcagagt ggctctgcta tcatgccttc actgtcaaac tgtcaaacca caaagttgtt    3780
tacaaatgct tgcttaagcc cctgaagttc tgtatgacac agctattccg gaagatccca    3840
aaggatacta aggcactact gaagacagtg acagaaccat ctatttgtca agatttcaaa    3900
gctatcctgg actga                                                    3915

<210> SEQ ID NO 4
<211> LENGTH: 18
<212> TYPE: DNA
<213> ORGANISM: Saccharomyces cerevisiae

<400> SEQUENCE: 4
tagggataac agggtaat                                                      18

<210> SEQ ID NO 5
<211> LENGTH: 18
<212> TYPE: DNA
```

-continued

```
<213> ORGANISM: Saccharomyces cerevisiae

<400> SEQUENCE: 5
atccctattg tcccatta                                                 18
```